(12) United States Patent
Imperiali et al.

(10) Patent No.: US 8,440,835 B2
(45) Date of Patent: May 14, 2013

(54) ENVIRONMENTALLY SENSITIVE FLUOROPHORES

(75) Inventors: Barbara Imperiali, Cambridge, MA (US); Galen S. Loving, Somerville, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 504 days.

(21) Appl. No.: 12/449,785

(22) PCT Filed: Feb. 26, 2008

(86) PCT No.: PCT/US2008/002485
§ 371 (c)(1),
(2), (4) Date: Feb. 17, 2010

(87) PCT Pub. No.: WO2008/106104
PCT Pub. Date: Sep. 4, 2008

(65) Prior Publication Data
US 2010/0168428 A1    Jul. 1, 2010

Related U.S. Application Data

(63) Continuation-in-part of application No. 11/710,789, filed on Feb. 26, 2007, now abandoned.

(51) Int. Cl.
*C07D 219/06* (2006.01)
(52) U.S. Cl.
USPC .......................................... 548/103
(58) Field of Classification Search ............ 546/103
See application file for complete search history.

(56) References Cited

U.S. PATENT DOCUMENTS

| | | | |
|---|---|---|---|
| 5,118,499 A | 6/1992 | Theodoropulos | |
| 5,854,275 A | 12/1998 | Robinson | |
| 5,912,137 A | 6/1999 | Tsien et al. | |
| 6,310,211 B1 | 10/2001 | Vaillancourt et al. | |
| 6,906,194 B2 | 6/2005 | Imperiali et al. | |
| 7,262,282 B2 | 8/2007 | Imperiali et al. | |
| 7,442,529 B2 | 10/2008 | Imperiali et al. | |
| 7,589,209 B2 | 9/2009 | Canary et al. | |
| 7,892,775 B2 | 2/2011 | Imperiali et al. | |
| 7,964,729 B2 | 6/2011 | Imperiali et al. | |
| 2005/0080242 A1 | 4/2005 | Imperiali et al. | |
| 2005/0080243 A1 | 4/2005 | Imperiali et al. | |
| 2005/0227365 A1 | 10/2005 | Canary et al. | |
| 2006/0135746 A1 | 6/2006 | Hosahudya et al. | |
| 2006/0205760 A1 | 9/2006 | Hartsel et al. | |
| 2006/0234206 A1 | 10/2006 | Imperiali et al. | |
| 2007/0196860 A1 | 8/2007 | Gee et al. | |
| 2008/0009026 A1 | 1/2008 | Gee | |
| 2008/0050761 A1 | 2/2008 | Imperiali et al. | |
| 2008/0085529 A1 | 4/2008 | Imperiali et al. | |
| 2008/0206885 A1 | 8/2008 | Imperiali et al. | |
| 2009/0082577 A1 | 3/2009 | Imperiali et al. | |
| 2011/0053180 A1 | 3/2011 | Imperiali et al. | |
| 2011/0281290 A1 | 11/2011 | Imperiali et al. | |

FOREIGN PATENT DOCUMENTS

| | | |
|---|---|---|
| CN | 1049232 C | 2/2000 |
| JP | 11335354 A | 12/1999 |
| JP | 2006213615 A | 8/2006 |
| WO | WO 01/44274 A1 | 6/2001 |
| WO | WO 2004/007461 A1 | 1/2004 |
| WO | WO 2005/037859 A2 | 4/2005 |
| WO | WO 2005/059163 A2 | 6/2005 |
| WO | WO 2006/094116 | 9/2006 |
| WO | WO 2008/016762 A1 | 2/2008 |
| WO | WO 2008/106104 A3 | 9/2008 |
| WO | WO 2008/144223 A2 | 11/2008 |
| WO | WO 2009/000965 A1 | 12/2008 |

OTHER PUBLICATIONS

Zhang, et al. (Document No. 139:197692, CAPLUS), entered in STN on Feb. 19, 2003.*
Su, et al. (Document No. 124:18002, CAPLUS) entered in STN in 1995.*
International Search Report and Written Opinion for International Patent Application No. PCT/US2007/076959 mailed Oct. 7, 2008.
International Preliminary Report on Patentability for Application No. PCT/US2007/076959 mailed Mar. 12, 2009.
Supplementary European Search Re sort for Application No. 07872278.2 dated Apr. 7, 2011.
Invitation to Pay Additional Fees for Application No. PCT/US2008/002485 mailed Aug. 28, 2008.
International Search Report and Written Opinion for International Patent Application No. PCT/US2004/032733 Oct. 28, 2005.
International Preliminary Report on Patentability for Application No. PCT/US2004/032733 mailed Apr. 20, 2006.
International Search Report and Written Opinion for International Patent Application No. PCT/US2010/002384 mailed Dec. 16, 2010.
Office Action for U.S. Appl. No. 11/511,050 mailed Jun. 17, 2009.
Office Action for U.S. Appl. No. 11/511,050 mailed Jan. 28, 2010.
Office Action for U.S. Appl. No. 11/511,050 mailed Aug. 11, 2010.
Notice of Allowance for U.S. Appl. No. 11/511,050 mailed Jan. 27, 2011.
Office Action for U.S. Appl. No. 11/106,349 mailed Mar. 8, 2007.
Office Action for U.S. Appl. No. 11/106,349 mailed Aug. 22, 2007.
Notice of Allowance for U.S. Appl. No. 11/106,349 mailed Dec. 27, 2007.

(Continued)

*Primary Examiner* — Shawquia Young
(74) *Attorney, Agent, or Firm* — Wolf, Greenfield & Sacks, P.C.

(57) ABSTRACT

The present invention generally relates to environment-sensitive fluorophores, including environment-sensitive fluorophores for reporting protein/protein and peptide/protein interactions. In one aspect, the present invention is directed to compounds and salts thereof, compositions and methods useful in determining biological interactions. In some cases, the compounds of the present invention are environment-sensitive fluorophores that have spectroscopic behavior that may depend on factors such as the physicochemical properties of the surrounding environment. The compounds of the present invention can be used, in certain embodiments, to monitor ions, small molecules, and biological processes such as protein folding, protein-protein interactions and phosphorylation events.

27 Claims, 25 Drawing Sheets

OTHER PUBLICATIONS

Notice of Allowance for U.S. Appl. No. 11/106,349 mailed Jun. 23, 2008.
Office Action for U.S. Appl. No. 10/681,427 mailed Sep. 15, 2004.
Notice of Allowance for U.S. Appl. No. 10/681,427 mailed Feb. 17, 2005.
Restriction Requirement for U.S. Appl. No. 10/819,587 mailed Jul. 13, 2006.
Office Action for U.S. Appl. No. 10/819,587 mailed Oct. 18, 2006.
Notice of Allowance for U.S. Appl. No. 10/819,587 mailed Feb. 13, 2007.
Office Action for U.S. Appl. No. 11/801,921 mailed Oct. 8, 2009.
Notice of Allowance for U.S. Appl. No. 11/801,921 mailed Apr. 2, 2010.
Notice of Allowance for U.S. Appl. No. 11/801,921 mailed Oct. 6, 2010.
[No Author Listed] A list of peptides that can be phosphorylated (and the corresponding Kinases) found at online at www.neb.com/neb/tech/tech_resource/protein_tools/substraye_recognition.html. Last Accessed on Sep. 26, 2003.
Barluenga et al., Easy and regioselective synthesis of highly functionalized o-quinodimethide precursors from fischer carbene complexes and Isocyanides. Chem. Eur. J. 2002; 8(18):4149-4163.
Blake et al., A new pyridine-based 12-membered macrocycle functionalised with different fluorescent subunits; coordination chemistry towards Cu(II), Zn(II), Cd(II), Hg(II), and Pb(II). Dalton Trans. Sep. 7, 2004;(17):2771-9. Epub Aug. 6, 2004.
Carrigan et al., The engineering of membrane-permeable peptides. Anal Biochem. Jun. 15, 2005;341(2):290-8.
Chen et al., Biosensors of protein kinase action: from in vitro assays to living cells. Biochim Biophys Acta. Mar. 11, 2004;1697(1-2):39-51.
Chen et al., Design and synthesis of a fluorescent reporter of protein kinase activity. J Am Chem Soc. Apr. 17, 2002;124(15:3840-1.
Goncalves, Fluorescent labeling of biomolecules with organic probes. Chem Rev. Jan. 2009;109(1):190-212.
Gonzalez-Vera et al., Synthesis of red-shifted 8-hydroxyquinoline derivatives using click chemistry and their incorporation into phosphorylation chemosensors. J Org Chem. Oct. 2, 2009;74(19):7309-14.
Gopi et al., Structural determinants for affinity enhancement of a dual antagonist peptide entry inhibitor of human immunodeficiency virus type-1. J Med Chem. May 8, 2008;51(9):2638-47.
Higashi et al., Imaging of cAMP-dependent protein kinase activity in living neural cells using a novel fluorescent substrate. FEBS Lett. Sep. 1, 1997;414(1):55-60.
Hofmann et al., Fluorescent monitoring of kinase activity in real time: development of a robust fluorescence-based assay for Abl tyrosine kinase activity. Bioorg Med Chem Lett. Dec. 17, 2001;11(24):3091-4.
Jotterand et al., Asymmetric synthesis of a new 8-hydroxyquinoline-derived alpha-amino acid and its incorporation in a peptidylsensor for divalent zinc. J Org Chem. May 4. 2001;66(9):3224-8.
Knor et al., Synthesis of novel 1,4,7,10-tetraazacyclodecane-1,4,7,10-tetraacetic acid (DOTA) derivatives for chemoselective attachment to unprotected polyfunctionalized compounds. Chem Eur J. 2007;13(21):6082-6089.
Kurokawa et al., A pair of fluorescent resonance energy transfer-based probes for tyrosine phosphorylation of the CrkII adaptor protein in vivo. J Biol Chem. Aug. 17, 2001;276(33):31305-10. Epub Jun. 13, 2001.
Lawrence, Chemical probes of signal-transducing proteins. Acc Chem Res. Jun. 2003;36(6):401-9.
Lee et al., Synthesis of 2,3,8-trisubstituted 7H-Isoindolo[5,6-g]quinoxaline-5,7,9,11(8H)-tetraones. Heterocycles. 2004;63(4):819-826.
Lindgren et al., Cell-penetrating peptides. Trends Pharmacol Sci. Mar. 2000;21(3):99-103.
Lukovic et al., Recognition-domain focused chemosensors: versatile and efficient reporters of protein kinase activity. J Am Chem Soc. Sep. 24, 2008;130(38):12821-7. Epub Aug. 29, 2008.

McLlroy et al., A continuous fluorescence assay for protein kinase C. Anal Biochem. May 15, 1991;195(1):148-52.
Moder et al., Defined dimensional alterations in enzyme substrates. Synthesis and enzymatic evaluation of some lin-naphthopurines. J. Am. Chem. Soc. 1982;104:2613-2624.
Montes et al., Effective manipulation of the electronic effects and its influence on the emission of 5-substituted tris(8-quinolinolate) aluminum(III) complexes. Chemistry. Jun. 2, 2006;12(17):4523-35.
Nagai et al., A fluorescent indicator for visualizing cAMP-induced phosphorylation in vivo. Nat Biotechnol. Mar. 2000;18(3):313-6.
Newton et al., Protein kinase C: structural and spatial regulation by phosphorylation, cofactors, and macromolecular interactions. Chem Rev. Aug 2001:(8):2353-64.
Nishikawa et al., Determination of the specific substrate sequence motifs of protein kinase C isozymes. J Biol Chem. Jan. 10, 1997;272(2):952-60.
Ohuchi et al., A fluorescent-labeled oligopeptide for monitoring PKA-mediated phosphorylation. Analyst. Nov. 2000;125(11):1905-7.
Okamoto et al., A supported epoxidation catalyst for nucleophilic olefins. Tetrahedron Letters. 1988;29(9):971-4. Abstract.
Pinna et al., Phosphorylated synthetic peptides as tools for studying protein phosphatases. Biochim Biophys Acta. Jul. 21, 1994;1222(3):415-31.
Post et al., A genetically engineered, protein-based optical biosensor of myosin II regulatory light chain phosphorylation. J Biol Chem. Apr. 29, 1994;269(17):12880-7.
Pozarentzi et al., The first benzodiazepine o-quinodimethane: generation and Diels-Alder reactions. Tetrahedron Letters. 2003;44:2007-9.
Rothmann et al., Chemical approaches for investigating phosphorylation in signal transduction networks. Trends Cell Biol. Sep. 2005;15(9):502-10.
Royzen et al., A sensitive probe for the detection of Zn(II) by time-resolved fluorescence. J Am Chem Soc. Mar. 29, 2006;128(12):3854-5.
Sainlos et al., Synthesis of anhydride precursors of the environment-sensitive fluorophores 4-DMAP and 6-DMN. Nat Protoc. 2007;2(12):3219-25.
Sainlos et al., Tools for investigating peptide-protein interactions: peptide incorporation of environment-sensitive fluorophores via on-resin derivatization. Nat Protoc. 2007;2(12):3201-9.
Sainlos et al., Tools for investigating peptide-protein interactions: peptide incorporation of environment-sensitive fluorophores through SPPS-based 'building block' approach. Nat Protoc. 2007;2(12):3210-8.
Sato et al., Fluorescent indicators for imaging protein phosphorylation in single living cells. Nat Biotechnol. Mar. 2002;20(3):287-94.
Shults et al., Optimal Sox-based fluorescent chemosensor design for serine/threonine protein kinases. Anal Biochem. May 15, 2006;352(2):198-207. Epub Mar. 20, 2006.
Shults et al., A multiplexed homogeneous fluorescence-based assay for protein kinase activity in cell lysates. Nat Methods. Apr. 2005;2(4):277-83. Epub Mar. 23, 2005.
Shults et al., Modular and tunable chemosensor scaffold for divalent zinc. J Am Chem Soc. Sep. 3, 2003;125(35):10591-7.
Shults et al., Versatile fluorescence probes of protein kinase activity. J Am Chem Soc. Nov. 26, 2003;125(47):14248-9.
Stevenson et al., Defined dimensional alterations in enzyme substrates. lin-naphthoadenine and lin-naphthoadenosine. J. Org. Chem. 1984;49:2158-2164.
Su et al., Syntheses and Metal Ion Complexation of Novel 8-Hydroxyquinoline-Containing Diaza-18-Crown-6 Ligands and Analogues. J Org Chem. Nov. 26, 1999;64(24):8855-8861.
Suzuki et al., Preparation and crystal structures of tetracyanoquinodimethans fused with [1,2,5]selenadiazole units. Chemistry Letters. 1987:2285-2288.
Ting et al., Genetically encoded fluorescent reporters of protein tyrosine kinase activities in living cells. Proc Natl Acad Sci U S A. Dec. 18, 2001;98(26):15003-8.
Venkatraman et al., Fluorogenic probes for monitoring peptide binding to class II MHC proteins in living cells. Nature Chemical Biology. Apr. 2007; 3 (4): 222-228.

Violin et al., A genetically encoded fluorescent reporter reveals oscillatory phosphorylation by protein kinase C. J Cell Biol. Jun. 9, 2003;161(5):899-909. Epub Jun. 2, 2003.

Wadia et al., Protein transduction technology. Curr Opin Biotechnol. Feb. 2002;13(1):52-6.

Walkup et al., Stereoselective synthesis of florescent a-amino acids containing oxine (8-hydroxyquinoline and their peptide incorporation in chemosensors for divalent zinc. J Org Chem. 1998; 63(19):6727-6731.

Wang et al., Self-reporting fluorescent substrates of protein tyrosine kinases. J Am Chem Soc. Feb. 15, 2006;128(6):1808-9.

Wright et al., Fluorometric assay for adenosine 3',5'-cyclic monophosphate-dependent protein kinase and phosphoprotein phosphatase activities. Proc Natl Acad Sci U S A..1981 ct;78(10):6048-50.

Yeh et al., Real time visualization of protein kinase activity in living cells. J Biol Chem. Mar. 29, 2002;277(13):11527-32. Epub Jan. 14, 2002.

Zhang et al., Genetically encoded reporters of protein kinase A activity reveal impact of substrate tethering. Proc Natl Acad Sci U S A. Dec. 18, 2001;98(26):14997-5002.

International Search Report and Written Opinion of the International Searching Authority for International Patent Application Serial No. PCT/US2008/002485 mailed Nov. 17, 2008.

Brown et al., "Matrix metalloproteinase inhibitors containing a (carboxyalkyl)amino zinc ligand: Modification of the P1 and P2 Residues," *J. Med Chem.*, (1994), 37:674-688.

Cacialli et al., "Naphthalimide side-chain polymers for organic light-emitting diodes: Band-offset engineering and role of polymer thickness," *J. Appl. Phys.*, (Feb. 15, 1998), 83(4):2343-2356.

Cohen et al., "Probing protein electrostatics with a synthetic fluorescent amino acid", *Science*, (May 31, 2002), 296:1700-1703.

Grabchev et al., "Synthesis and properties of fluorescent 1,8-Naphthalimide dyes for application in liquid crystal displays," *J. Mater. Chem.*, (Nov. 19, 1999), 2000, 10:1291-1296.

Pantoja, et al. "Synthesis and use of fluorescent molecular probes for measuring cell-surface enzymatic oxidation of amino acids and amines in seawater," *Analytical Biochemistry*, (1993), 211:210-218.

Vazquez et al., "Photophysics and biological applications of the enviornment sensitive fluorophore 6-N,N-Dimethylamineo-2,3-naphthalimide," *JACS*, (2005), 127:1300-1306.

Vazquez et al., "A new environment-sensitive fluorescent amino acid for Fmoc-based solid phase peptide synthesis," *Org. Biomol. Chem.*, (2004), 2:1965-1966.

Wang et al., "Phosphorylation-driven protein-protein interactions: a protein kinase sensing system," *J. Am. Chem. Soc.*, (2005), 127:7684-7685.

Weber et al., "Synthesis and spectral properties of a hydrophobic fluorescent probe: 6-propionyl-2-(dimethylamino)naphthalene," *Biochemistry*, (1979), 18(14):3075-3078.

Zhang, et al. "New fluorescent conjugates of uridine nucleoside and substituted 1,8-naphthalimide: Synthesis, weak interactions and solvent effects on spectra," *Monatshefte fur Chemie Chemical Monthly*, (2003), 134:393-402.

International Preliminary Report on Patentability for International Application No. PCT/US2008/002485 mailed Aug. 26, 2009.

Written Opinion of the International Searching Authority for International Application No. PCT/US2008/002485 mailed Aug. 26, 2009.

* cited by examiner

Dap(6-DMN)
$\lambda_{ex}$ 375 nm
$\lambda_{em}$ 460-595 nm

Dap(4-DMN)
$\lambda_{ex}$ 445 nm
$\lambda_{em}$ 492-538 nm

DANSYL

NBD

4DMAP

6DMN

4DMN

N-α-Fmoc-(4-N,N-dimethylamino-1,8-naphthalimido) alanine
(Fmoc-4DMNA)

4-N,N-dimethylamino-N-[2-bromoacetamido]-1,8-naphthalimide

4-N,N-dimethylamino-N-(2-maleimidyl-ethyl)-1,8-naphthalimide

4-N,N-dimethylamino-N-[2-(2-bromo-acetylamino)-ethyl]-1,8-naphthalimide

4-*N,N*-dimethylamino-*N*-[2-(2-maleimidyl-ethoxy)-ethyl]-1,8-naphthalimide

*N*-α-Fmoc-(4-*N,N*-dimethylamino-1,8-naphthalimido) alanine (Fmoc-4DMNA)

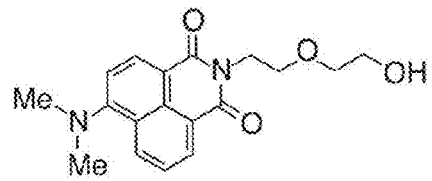
4-N,N-dimethylamino-N-[2-(2-hydroxy-ethoxy)-ethyl]-1,8-naphthalimide (8)
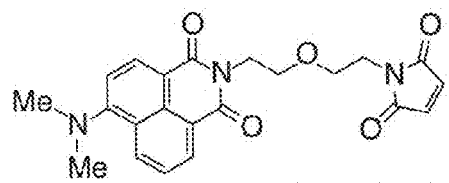
4-N,N-dimethylamino-N-[2-(2-maleimidyl-ethoxy)-ethyl]-1,8-naphthalimide (9)
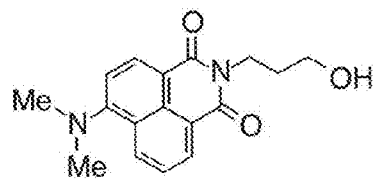
4-N,N-dimethylamino-N-(3-hydroxy-propyl)-1,8-naphthalimide (6)
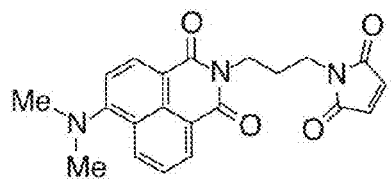
4-N,N-dimethylamino-N-(3-maleimidyl-propyl)-1,8-naphthalimide (7)
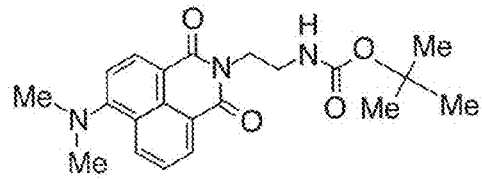
4-N,N-dimethylamino-N-(2-tert-butoxycarbonylamino-ethyl)-1,8-naphthalimide (2)
Fig. 12B-1

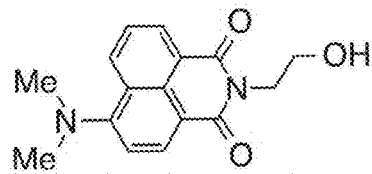
4-*N,N*-dimethylamino-*N*-(2-hydroxy-ethyl)-1,8-naphthalimide (4)
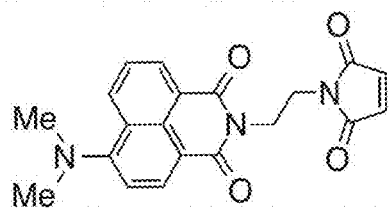
4-*N,N*-dimethylamino-*N*-(2-maleimidyl-ethyl)-1,8-naphthalimide (5)
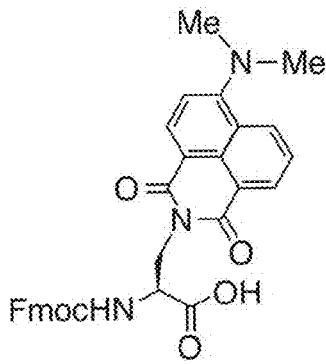
*N*-α-Fmoc-(4-*N,N*-dimethylamino-1,8-naphthalimido) alanine (12)
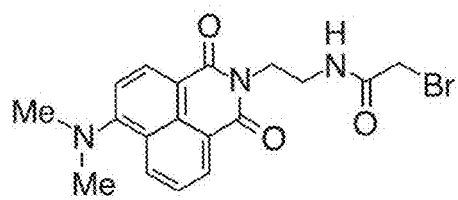
4-*N,N*-dimethylamino-*N*-[2-(2-bromo-acetylamino)-ethyl]1,8-naphthalimide (3)
Fig. 12B-2

M13 PEPTIDE PROBE: (H$_2$N)-RRWKKN-(4DMNA)-IAVSAANRFKK-(CONH$_2$) (SEQ ID NO: 13)

ETHYL LINKER

PEG LINKER

Ca$^{2+}$/LABELED M146C CaM MUTANT/
M13 PEPTIDE COMPLEX

SEQUENCE LISTING

```
<160> NUMBER OF SEQ ID NOS: 13

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Xaa is Dap(4-DMN)

<400> SEQUENCE: 1

Ile Asn Pro His Asp Tyr Gln Xaa Glu
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Xaa is Dap(4-DMN)

<400> SEQUENCE: 2

Ile Asn Pro His Asp Tyr Gly Xaa Glu
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Xaa is Dap(4-DMN)

<400> SEQUENCE: 3

Ser Gln Val Asn Glu Tyr Gly Xaa Glu
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<222> LOCATION: (7)..(7)
<223> OTHER INFORMATION: Xaa is Dap(4-DMN)

<400> SEQUENCE: 4

Ser Gln Val Asn Glu Tyr Xaa Glu
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is -NH-CH[CH2(Dansyl)]-C(=O)-

<400> SEQUENCE: 5

Lys Arg Arg Xaa Lys Lys
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is -NH-CH[CH2(NDB)]-C(=O)-

<400> SEQUENCE: 6

Lys Arg Arg Xaa Lys Lys
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is -NH-CH[CH2(4DMAP)]-C(=O)-

<400> SEQUENCE: 7

Lys Arg Arg Xaa Lys Lys
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: Xaa is -NH-CH[CH2(6DMN)]-C(=O)-

<400> SEQUENCE: 8

Lys Arg Arg Xaa Lys Lys
1               5
```

```
<210> SEQ ID NO 9
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is -NH-CH[CH2(4DMN)]-C(=O)-

<400> SEQUENCE: 9

Lys Arg Arg Xaa Lys Lys
1               5

<210> SEQ ID NO 10
<211> LENGTH: 18
<212> TYPE: PRT
<213> ORGANISM: Artificial Sequence
<220> FEATURE:
<223> OTHER INFORMATION: Synthetic peptide

<400> SEQUENCE: 10

Arg Arg Trp Lys Lys Asn Phe Ile Ala Val Ser Ala Ala Asn Arg Phe
1               5                   10                  15

Lys Lys

<210> SEQ ID NO 11
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 11

Tyr Asp His Pro
1

<210> SEQ ID NO 12
<211> LENGTH: 4
<212> TYPE: PRT
<213> ORGANISM: Artificial Sequence
<220> FEATURE:
<223> OTHER INFORMATION: Synthetic peptide

<400> SEQUENCE: 12

Tyr Glu Asn Val
1

<210> SEQ ID NO 13
<211> LENGTH: 18
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (7)..(7)
<223> OTHER INFORMATION: Xaa is 4DMNA

<400> SEQUENCE: 13

Arg Arg Trp Lys Lys Asn Xaa Ile Ala Val Ser Ala Ala Asn Arg Phe
1               5                   10                  15

Lys Lys
```

US 8,440,835 B2

ENVIRONMENTALLY SENSITIVE FLUOROPHORES

RELATED APPLICATIONS

This application is a national-stage application under 35 U.S.C. §371 of International Patent Application No. PCT/US2008/002485, filed Feb. 26, 2008, entitled "Environmentally Sensitive Fluorophores," by Imperiali, et al., which is a continuation-in-part of U.S. patent application Ser. No. 11/710,789, filed Feb. 26, 2007, entitled "Environmentally Sensitive Fluorophores," by B. Imperiali, et al., each of which is incorporated herein by reference.

GOVERNMENT FUNDING

Research leading to various aspects of the present invention were sponsored, at least in part, by the National Science Foundation, grant number CHE0414243 and by the National Institutes of Health, grant number GM064346. The U.S. Government has certain rights in this invention.

FIELD OF INVENTION

The present invention generally relates to environment-sensitive fluorophores, including environment-sensitive fluorophores for reporting protein/protein and peptide/protein interactions.

BACKGROUND

Fluorescence is the result of a three-stage process that occurs when certain molecules absorb energy. The three stages comprise: 1) excitation; 2) excited-state lifetime; and 3) fluorescence emission. During stage 1, excitation, a photon of a certain energy is absorbed by the fluorophore. The fluorophore is initially in its ground state ($S_0$). Absorption of the photon causes that fluorophore to become excited. The energy of the absorbed photon is transferred to an electron. The electron is transferred to a higher energy state. The fluorophore exists in an excited electronic singlet state ($S_1$), also called an excited state. The excited state of the fluorophore exists for a finite time, typically $10^{-8}$ to $10^{-9}$ seconds. During the excited state, the fluorophore changes in its translational, vibrational, and electronic energy states, and is subject to interactions with its molecular environment. The excited fluorophore releases energy and returns to the ground state, $S_0$, by fluorescence emission. Other processes such as fluorescence energy transfer, intersystem crossing, and collisional quenching may also depopulate $S_1$. The ratio of the number of fluorescence photons emitted, during the emission stage, to the number of photons absorbed, during the excitation stage, is termed the quantum yield. The quantum yield is a measure of the efficiency of fluorescence in competition with other processes such as fluorescence energy transfer, intersystem crossing, and collisional quenching.

During the third stage, fluorescence emission, a photon of energy hv (where h is Planck's constant and v is the frequency of the photon) is emitted, returning the fluorophore to its ground state $S_0$. The energy of the emitted photon is lower than the energy of the photon absorbed during the excitation stage. The difference in energy can be attributed to dissipation through processes during the excited-state lifetime, such processes include fluorescence energy transfer, intersystem crossing, and collisional quenching. The difference in energy of the absorbed photon and the emitted photon is called the Stokes shift. The Stokes shift is fundamental to the sensitivity of fluorescence techniques because it allows emission photons to be detected against a low background, and at a different wavelength than the excitation photons.

Compounds that have fluorescent properties have numerous uses. Fluorescent molecules can be used in single molecule spectroscopy, liquid crystal displays, light emitting diodes, solar energy collectors, and laser active media. Fluorescent molecules whose spectra or quantum yields are sensitive to their environments are valuable as fluorescent dyes and in the study of heterogeneous media, organized media, and biological media.

Environment-sensitive fluorophores are a special class of chromophores that have spectroscopic behavior that is dependent on the physicochemical properties of the surrounding environment. Solvatochromic fluorophores display sensitivity to the polarity of the local environment. These molecules exhibit a low quantum yield in aqueous solution, but become highly fluorescent in nonpolar solvents or when bound to hydrophobic sites in proteins or membranes. Examples of solvatochromic fluorophores include 2-propionyl-6-dimethylaminonaphthalene (PRODAN) (Weber et al. *Biochemistry* 1979, 18, 3075-3078; Cohen et al. *Science* 2002, 296, 1700-1703), 4-dimethylamino phthalimide (4-DMAP) (Saroja et al. *J. Fluoresc.* 1998, 8, 405-410), and 4-amino-1,8-naphthalimide derivatives (Grabchev et al. *J. Photochem. Photobiol., A* 2003, 158, 37-43; Martin et al. *J. Lumin.* 1996, 68, 157-146). Although PRODAN and its derivatives are widely used, these probes have limitations resulting from the relatively intense fluorescence even in aqueous environments. Thus, there is a need for alternate compounds.

U.S. Patent Application Publication No. 2006/0234206 discloses a 6-dimethylaminonaphthalimide group as an environment-sensitive fluorophore for reporting protein/protein and peptide/protein interactions. The fluorophore is integrated as part of an amino acid termed Dap(6-DMN). U.S. Patent Application Publication No. 2006/0205760, to Hartsel et al., discloses a naphthalimide compound with a mono-substituted amino group at the 4 position. Hartsel does not disclose an amino acid motif as an imide substitutent.

SUMMARY OF THE INVENTION

The present invention generally relates to environment-sensitive fluorophores. The subject matter of the present invention involves, in some cases, interrelated products, alternative solutions to a particular problem, and/or a plurality of different uses of one or more systems and/or articles.

The fluorophore compounds disclosed in some aspects of the present invention have improved photophysical properties as an environment-sensitive reporter and/or improved chemical stability for biomolecule labeling and the detection of protein/protein and peptide/protein interactions.

In one aspect, the present invention provides compounds of formula (I):

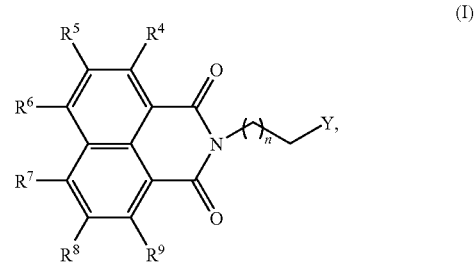

wherein $R^4$, $R^5$, $R^6$, $R^7$, $R^8$, $R^9$, n, and Y are as defined below. One example compound (VI) referred to as Dap(4-DMN) is disclosed.

In another aspect, the present invention also provides peptides containing compound (I), or any other compound as described herein. In yet another aspect, the present invention also provides a peptide comprising an amino acid residue, where a side chain of the amino acid residue is modified with a compound of formula (VII):

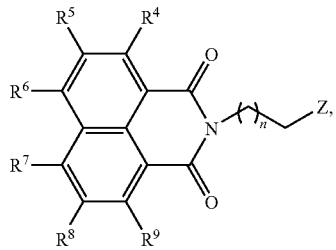

where $R^4$, $R^5$, $R^6$, $R^7$, $R^8$, $R^9$, n, and Z are as defined below. In still another aspect, the present invention provides a peptide comprising an amino acid residue of formula (XIII):

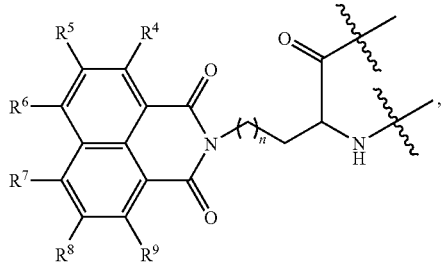

where $R^4$, $R^5$, $R^6$, $R^7$, $R^8$, $R^9$, and n are as defined below.

In one set of embodiments, the invention includes a compound of formula (I):

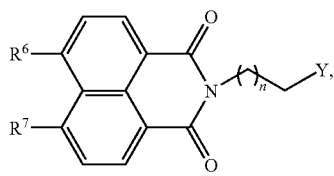

where at least one of $R^6$ and $R^7$ is —$NR^1R^2$, $R^1$ and $R^2$ each independently being a substituted or unsubstituted alkyl; Y is a halogen, —SH, —$NHR^3$, —C(O)X, -maleimidyl, —NH-$COR^3$, —NHCO(CH$_2$)X, or —CH(NHR$^3$)COOH; $R^3$ is hydrogen, substituted or unsubstituted alkyl, or an N-protecting group; X is hydrogen, halogen, hydroxy, alkoxy, or O-succidimidyl; and n is 0, 1, 2, or 3.

The invention, according to another aspect, includes N-alpha-Fmoc-(4-N,N-dimethylamino-1,8-naphthalimido) alanine.

In another set of embodiments, the invention includes a peptide having an amino acid residue having a side chain modified by reaction with a compound of formula (VII):

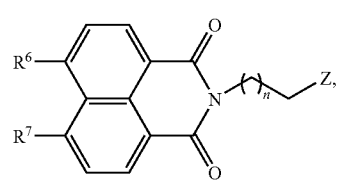

where at least one of $R^6$ and $R^7$ is —$NR^1R^2$, $R^1$ and $R^2$ each independently being a substituted or unsubstituted alkyl; Z is halogen, —SH, —$NHR^3$, —C(O)X, -maleimidyl, —NH-$COR^3$, or —NHCO(CH$_2$)X; $R^3$ is hydrogen, substituted or unsubstituted alkyl, or an N-protecting group; is hydrogen, halogen, hydroxy, alkoxy, or O-succidimidyl; and n is 0, 1, 2, or 3.

According to another set of embodiments, the invention includes a peptide comprising a modified amino acid residue of formula (XIII):

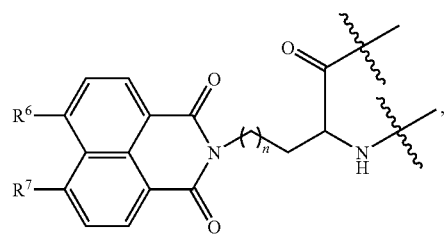

where at least one of $R^6$ and $R^7$ is —$NR^1R^2$, $R^1$ and $R^2$ each independently being a substituted or unsubstituted alkyl, or $R^1$ and $R^2$ together with the nitrogen to which they are attached, form a substituted or unsubstituted 5- or 6-membered ring; and n is 0, 1, 2, or 3.

In yet another aspect, the invention is a method. In one set of embodiments, the method includes acts of contacting a peptide with a compound of formula (VII):

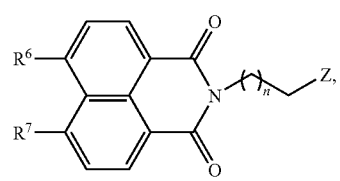

where at least one of $R^6$ and $R^7$ is —$NR^1R^2$, $R^1$ and $R^2$ each independently being a substituted or unsubstituted alkyl; Z is halogen, —SH, —$NHR^3$, —C(O)X, -maleimidyl, —NH-$COR^3$, or —NHCO(CH$_2$)X; $R^3$ is hydrogen, substituted or unsubstituted alkyl, or an N-protecting group; X is hydrogen, halogen, hydroxy, alkoxy, or O-succidimidyl; and n is 0, 1, 2, or 3.

According to another set of embodiments, the method includes acts of contacting a peptide with a compound of formula (VII):

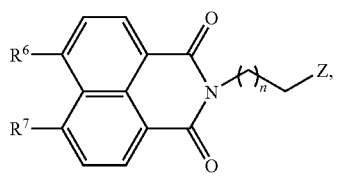
(VII)

where at least one of $R^6$ and $R^7$ is —$NR^1R^2$, $R^1$ and $R^2$ each independently being a substituted or unsubstituted alkyl; Z is halogen, —SH, —$NHR^3$, —C(O)X, -maleimidyl, —NH-$COR^3$, or —$NHCO(CH_2)X$; $R^3$ is hydrogen, substituted or unsubstituted alkyl, or an N-protecting group; X is hydrogen, halogen, hydroxy, alkoxy, or O-succidimidyl; and n is 0, 1, 2, or 3.

The method, according to still another aspect, includes acts of coupling, to an amine, a compound of formula (XVI):

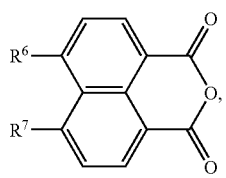
(XVI)

where at least one of $R^6$ and $R^7$ is —$NR^1R^2$, $R^1$ and $R^2$ each independently being a substituted or unsubstituted alkyl.

In another aspect, the present invention includes a compound of formula (XVI):

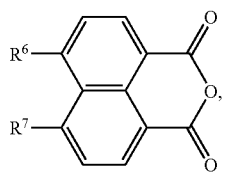
(XVI)

where at least one of $R^6$ and $R^7$ is —$NR^1R^2$, $R^1$ and $R^2$ each independently being a substituted or unsubstituted alkyl; Y is a halogen, —SH, —$NHR^3$, —C(O)X, -maleimidyl, —NH-$COR^3$, —$NHCO(CH_2)X$, or —$CH(NHR^3)COOH$; $R^3$ is hydrogen, substituted or unsubstituted alkyl, or an N-protecting group; and X is hydrogen, halogen, hydroxy, alkoxy, or O-succidimidyl.

In another set of embodiments, the present invention includes a compound of formula (XVIII):

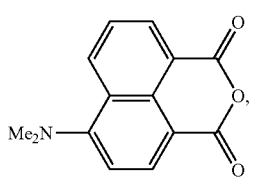
(XVIII)

According to yet another set of embodiments, the article includes a compound of formula (XIX) or (XX):

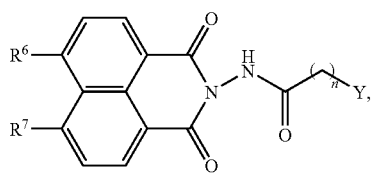
(XIX)

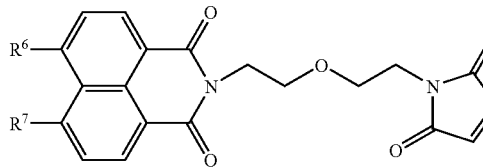
(XX)

where at least one of $R^6$ and $R^7$ is —$NR^1R^2$; $R^1$ and $R^2$ each independently being a substituted or unsubstituted alkyl; Y is a halogen, —SH, —$NHR^3$, —C(O)X, -maleimidyl, —NH-$COR^3$, —$NHCO(CH_2)X$, or —$CH(NHR^3)COOH$; $R^3$ is hydrogen, substituted or unsubstituted alkyl, or an N-protecting group; X is hydrogen, halogen, hydroxy, alkoxy, or O-succidimidyl; and n is 0, 1, 2, or 3.

In another aspect, the invention includes a compound of formula (XXI):

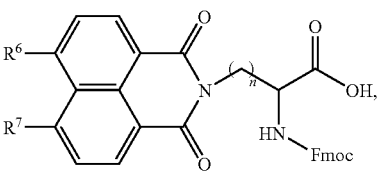
(XXI)

where at least one of $R^6$ and $R^7$ is —$NR^1R^2$; $R^1$ and $R^2$ each independently being a substituted or unsubstituted alkyl; and n is 0, 1, 2, or 3.

The present invention also provides a method for probing biological interactions using peptides containing the compound (I), or any of the compounds disclosed herein, according to another aspect.

In another aspect, the present invention is directed to a method of making one or more of the embodiments described herein, for example, an environment-sensitive fluorophore. In another aspect, the present invention is directed to a method of using one or more of the embodiments described herein, for example, an environment-sensitive fluorophore.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 12A-12B illustrate various compounds of the invention;

DETAILED DESCRIPTION

Figure 1A:
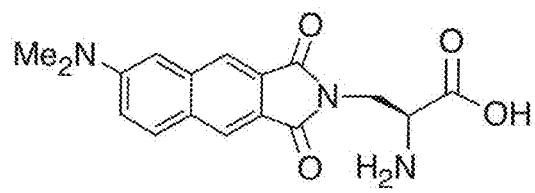
FIGS. 1A-1D illustrate the structures of the Dap(6-DMN) and Dap(4-DMN), the fluorescence excitation and emission maxima, and the changes in fluorescence spectra in methanol and dioxane for the two compounds, according to one embodiment of the invention.
Figure 1B:
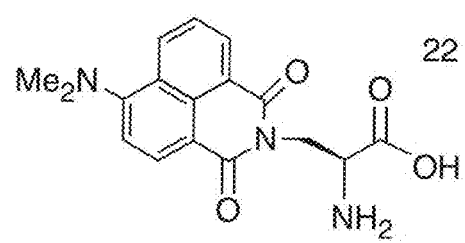

The present invention generally relates to environment-sensitive fluorophores, including environment-sensitive fluorophores for reporting protein/protein and peptide/protein interactions. In one aspect, the present invention is directed to compounds and salts thereof, compositions and methods useful in determining biological interactions. In some cases, the compounds of the present invention are environment-sensitive fluorophores that have spectroscopic behavior that may depend on factors such as the physicochemical properties of the surrounding environment. The compounds of the present invention can be used, in certain embodiments, to monitor ions, small molecules, and biological processes such as protein folding, protein-protein interactions and phosphorylation events.

Various aspects of the invention are directed to various environment-sensitive fluorophores. In some cases, the spectroscopic behavior of the fluorophores may depend on factors such as the physicochemical properties of the surrounding environment, for example, the polar/nonpolar nature of the surrounding environment. In certain cases, the fluorophores can be used to monitor ions, small molecules, or biological processes such as protein folding, protein-protein interactions, or phosphorylation events.

In one set of embodiments, the compositions of the present invention undergo enhanced fluorescence in nonpolar environments as compared to polar environments. Examples of nonpolar environments include nonpolar solvents, oils, hydrophobic proteins, or membranes. Without wishing to be bound by any theory, it is believed that various compositions of the present invention are able to fluoresce in nonpolar environments to a greater extent than in polar environments due to an internal charge transfer (ICT) process that occurs in the excited singlet state more efficiently in polar solvents. The ICT is generally believed to occur through the donation of a single electron from an amino moiety (e.g., a dimethylamino moiety) to the pi orbital system of the naphthalimide ring thereby creating a large charge separation in the overall system. This charge transfer may involve a subsequent twisting of the amino group such that the p-orbital of the amino group bearing a single unpaired electron is no longer in conjugation with the pi system of the naphthalimide ring. This may then reduce the pairing energy of the single electron now isolated in the pi system of the naphthalimide ring with that of the single electron now isolated on in the p-orbital of the amino moiety, thereby allowing the process of intersystem crossing (unpairing of the HOMO and LUMO electrons) to occur with greater efficiency. The process of intersystem crossing results in a new electronic excited state commonly referred to as the triplet state. The triplet state of most excited state systems is typically longer lived (~$10^{-3}$ seconds) compared to that of the excited singlet state ($10^{-8}$ to $10^{-9}$ seconds), which greatly enhances the probability of the system returning to the ground electronic state through competing rapid non-radiative processes.

Due to the large dipole that is produced by an ICT process, this electronic state is poorly stabilized in nonpolar environments (e.g. dioxane) and hence is unlikely to be populated upon irradiation. The system will therefore settle rapidly through internal conversion to what is commonly referred to as the local excited state (LE). The LE state is very short lived and typically returns to the ground electronic state through a fluorescence event.

In contrast, the ICT state is more stable in polar environments (particularly polar-protic environments like water) compared to the LE state and thus is more likely to be the populated state following initial excitation of the system. Since ICT is an efficient mechanism for fluorescence quenching, the fluorescence quantum yield of the system in this type of environment may greatly be reduced.

In one embodiment, a compound of the present invention is of formula (I):

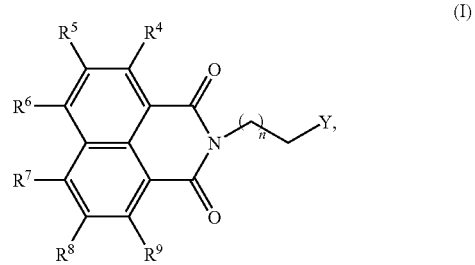

where $R^4$, $R^5$, $R^6$, $R^7$, $R^8$, and $R^9$ are each independently hydrogen, halogen, or alkyl, where at least one of $R^4$, $R^5$, $R^6$, $R^7$, $R^8$, and $R^9$ is —$NR^1R^2$, —OH, —SH, —$OR^1$, or —$SR^1$.

$R^1$ and $R^2$ are each independently substituted or unsubstituted alkyl, or $R^1$ and $R^2$ together with the nitrogen to which they are attached, form a substituted or unsubstituted 5- or 6-membered ring. Y may be a halogen, —SH, —NHR$^3$, —C(O)X, —maleimidyl, —NHCOR$^3$, —NHCO(CH$_2$)X, or —CH(NHR$^3$)COOH, and $R^3$ is hydrogen, substituted or unsubstituted alkyl, or an N-protecting group. X is hydrogen, halogen, hydroxy, alkoxy, or O-succidimidyl, and n is 0, 1, 2, or 3. In some cases, one of $R^6$ and $R^7$ is —NR$^1$R$^2$. $R^1$ or $R^2$ may be alkyl, or both $R^1$ and $R^2$ may be alkyl. In some embodiments, both $R^1$ and $R^2$ are methyl, ethyl or propyl. $R^1$ and $R^2$, together with the nitrogen to which they are attached may, in certain instances, be pyrrolidinyl, piperidinyl, or morpholinyl. $R^3$ may be an N-protecting group, such as Boc (di-tert-butyl dicarbonate), Cbz (carboxybenzyl), or Fmoc (9H-fluoren-9-ylmethoxycarbonyl). The compound can be a D-isomer or an L-isomer. In some cases, $R^4$, $R^5$, $R^8$, and $R^9$ are each —H.

An example of such a compound is formula (II):

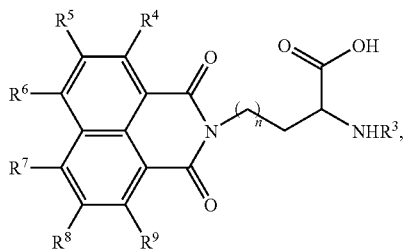

(II)

where n, $R^3$, $R^4$, $R^5$, $R^6$, $R^7$, $R^8$, and $R^9$ are as described above. As another example, the compound may be formula (III):

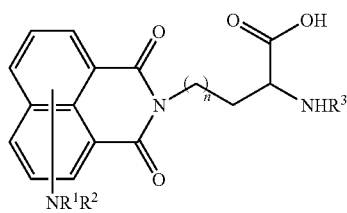

(III)

where —NR$^1$R$^2$ can substitute any open valence of any ring within structure (III); and n, $R^1$, $R^2$ and $R^3$ are as described above. As another example, the compound may have a formula (IV):

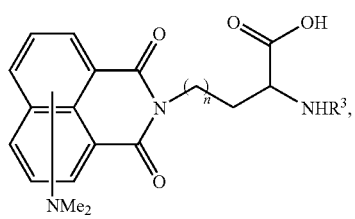

(IV)

where —NMe$_2$ can substitute any open valence of any ring within structure (IV); and n and $R^3$ are as described above. As yet another example, the compound may have a formula (V):

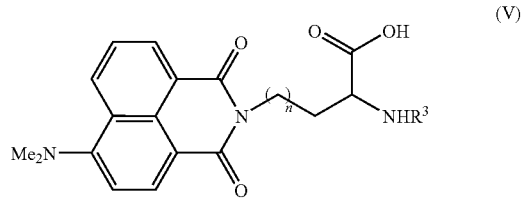

(V)

where n and $R^3$ are as described above. The compound, in another example, may have a formula (VI):

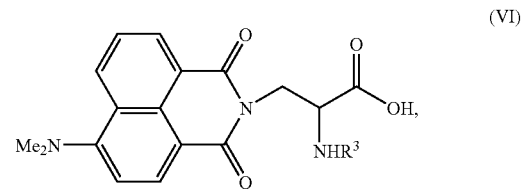

(VI)

where $R^3$ is as described above. In another example, the compound may have a formula (VII):

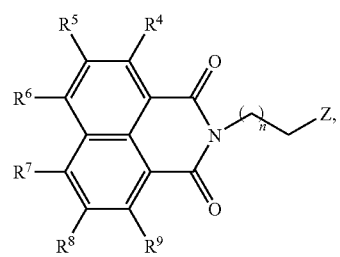

(VII)

where Z is halogen, —SH, —NHR$^3$, —C(O)X, -maleimidyl, or —NHCOR$^3$, —NHCO(CH$_2$)X and n, $R^4$, $R^5$, $R^6$, $R^7$, $R^8$, and $R^9$ are as described above. As yet another example, the compound may have a formula (VIII):

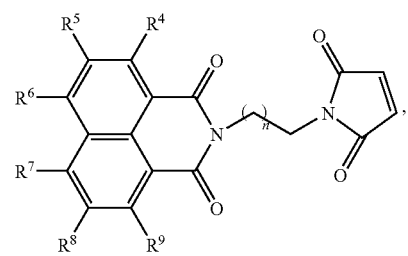

(VIII)

where n, $R^4$, $R^5$, $R^6$, $R^7$, $R^8$, and $R^9$ are as described above. As still another example, the compound may have a formula (IX):

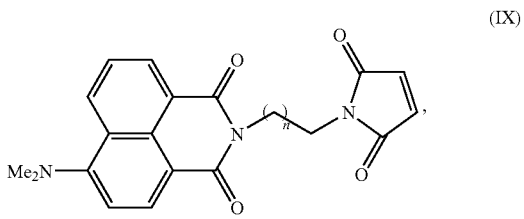

(IX)

where n is as described above. In another example, the compound may have a formula (X):

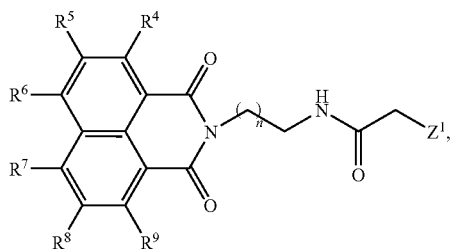
(X)

where $Z^1$ is halogen; and n, $R^4$, $R^5$, $R^6$, $R^7$, $R^8$, and $R^9$ are as described above. In yet another example, the compound may have a formula (XI):

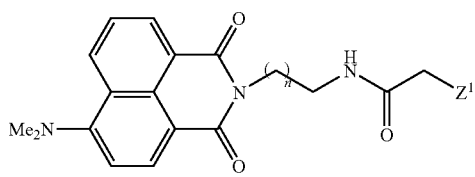
(XI)

where $Z^1$ and n are as described above. In still another example, the compound may have a formula (XII):

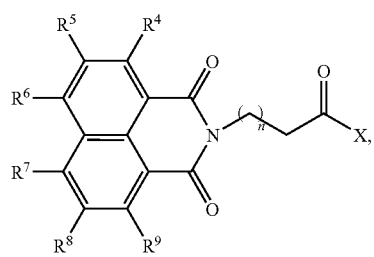
(XII)

where n, X, $R^4$, $R^5$, $R^6$, $R^7$, $R^8$, and $R^9$ are as described above. As another example the compound may have a formula such as (XIX), (XX), or (XXI):

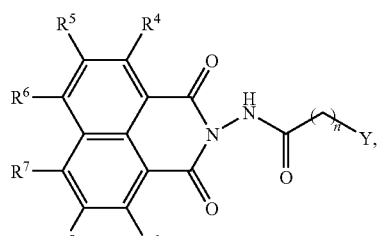
(XIX)

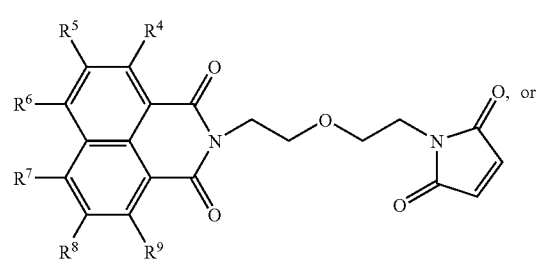
(XX)

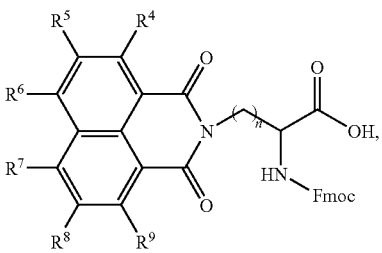
(XXI)

where n, X, $R^4$, $R^5$, $R^6$, $R^7$, $R^8$, and $R^9$ are as described above.

Other examples include, but are not limited to, anhydride forms of the above compounds. Non-limiting examples of such anhydrides include:

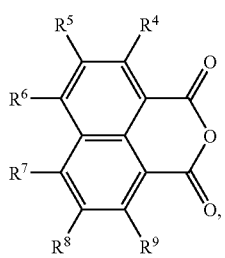
(XVI)

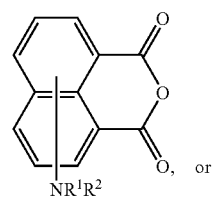
(XVII)

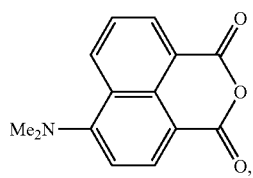
(XVIII)

where $R^4$, $R^5$, $R^6$, $R^7$, $R^8$, and $R^9$ are as described above.

Figure 12A:
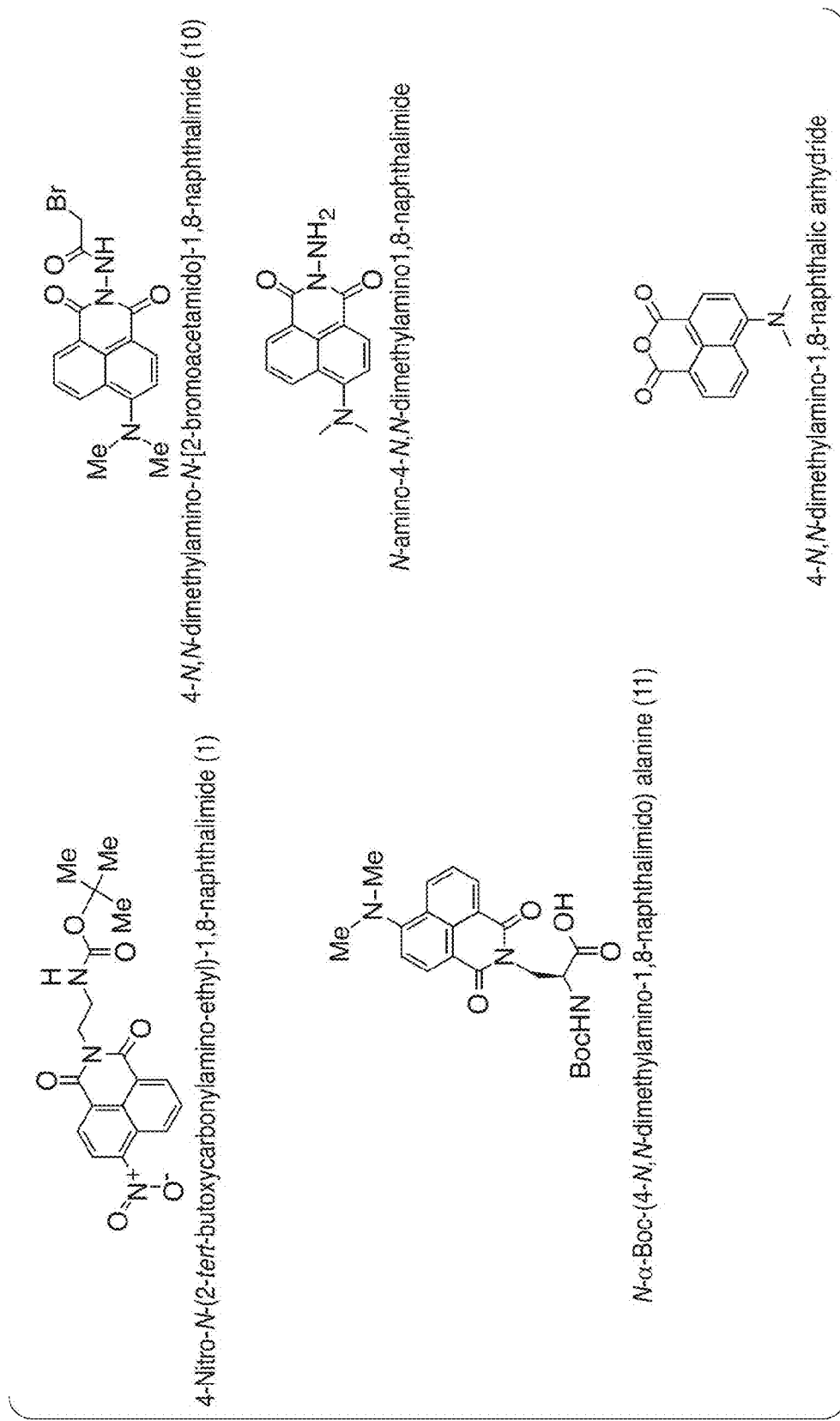

Yet other examples of compounds of the present invention are shown in FIG. 12.

Another aspect of the invention is generally directed to proteins or peptides incorporating moieties such as those described above. For instance, a peptide may be contacted with one of the above-described compounds, such that a reaction occurs. As specific examples, an amino acid residue on a protein, such as cysteine, aspartic acid, glutamic acid, or lysine, may be well-suited for reaction with a compound such as those described above. Such peptides, incorporating such compounds, may be useful for a wide variety of applications, as often, the compound remains fluorescent even when attached to the peptide. Examples of applications involving such peptides include as fluorescent probes for various biological applications, as discussed below.

As a specific example, fluorophore compounds such as formulae (II) and (VI), can be formed into peptides using standard peptide synthesis (solid phase or solution phase). Standard peptide synthesis is well-known in the art. See, for example, *Fmoc Solid Phase Peptide Synthesis—A Practical Approach*, Oxford University Press, 2003, Eds W. C. Chan and P. D. White (ISBN 0 19 963 724 5); and *The Chemical Synthesis of Peptides*, Clarendon Press, Oxford, 1994, Jones, J. (ISBN 0 19 855839 2).

Figure 2A:
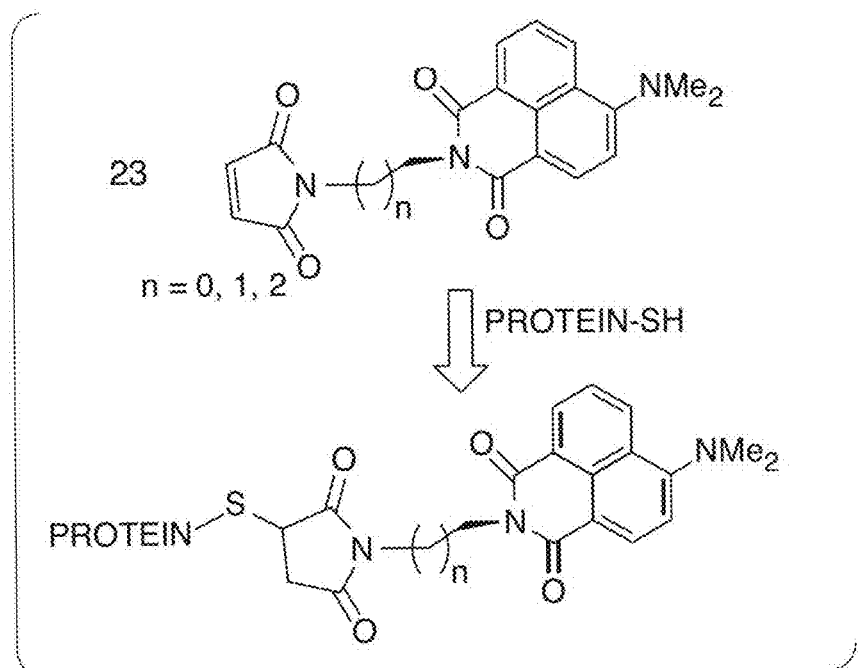
FIG. 2A-2B illustrate certain methods by which the fluorophore may be incorporated into compounds, such as 3 and 4, that can be used for the selective chemical modification of cysteine in intact peptides and proteins, in accordance with another embodiment of the invention.
Figure 2B:
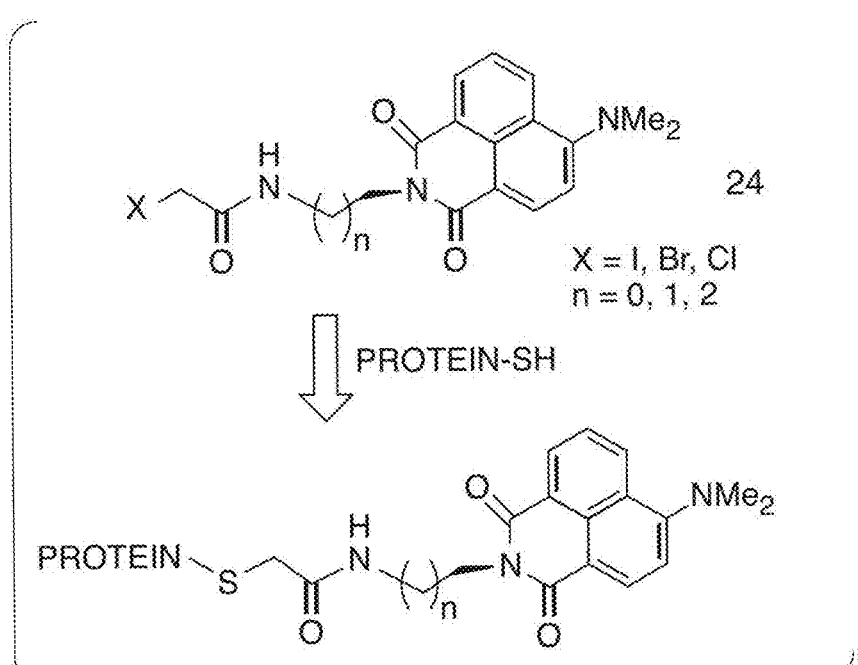

As another example, when the fluorophore compounds are coupled to peptide after synthesis, the peptide may be first synthesized and protecting groups on the side chains of the peptide can be selectively removed. Then the fluorophore compounds, such as formulae (VII), (IX) and (XI), can be coupled to the side chains of formed peptides using standard coupling methods. For example, when Y is a maleimidyl or an alpha-halo-amide, the compound can be coupled to a residue containing a thiol group in its side chain (such as Cys). An example of such a reaction is shown in FIG. 2A. As another example, when Y is a halogen, the compound can be coupled to a residue containing a thiol group in its side chain (such as Cys), forming a thioether linkage, as the example in FIG. 2B illustrates. As yet another example, when Y is an amine, it can be coupled to a residue containing a carboxylic acid in its side chain (such as Asp or Glu), forming an amide linkage. In another example, when Y is thiol, it can be coupled to a residue containing a thiol group in its side chain (such as Cys), forming a disulfide linkage. As still another example, when Y is a carboxylic acid, it can be coupled to a residue containing an amine in its side chain. In another example, when Y is an aldehyde, it can be coupled to a residue containing amine via reductive amination. The fluorophore-containing peptide may then be deprotected and purified in some cases.

Selective deprotection of amino acids is well known in the art. One method is to use orthogonal side-chain protection such as allyl (OAll) (for the carboxyl group in the side chain of glutamic acid or aspartic acid, for example), allyloxy carbonyl (Alloc) (for the amino nitrogen in the side chain of lysine or ornithine, for example), p-methoxytrityl (MMT) or acetamidomethyl (Acm) (for the sulfhydryl of cysteine). OAll and Alloc are easily removed by Pd, Acm can be removed by iodine treatment, and MMT can be removed by mild acid treatment.

Methods for introduction and removal of N-protecting groups are known to those skilled in the art, examples of which are disclosed in Greene and Wuts, Protective Groups in Organic Synthesis, 2nd ed.; John Wiley & Sons, New York, 1991.

As a non-limiting example, a peptide may be reacted with a compound of formula (VII):

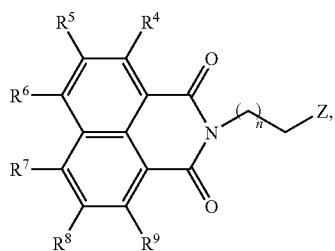

(VII)

where $R^4$, $R^5$, $R^6$, $R^7$, $R^8$, and $R^9$ are each independently hydrogen, halogen, or alkyl, and where at least one of $R^4$, $R^5$, $R^6$, $R^7$, $R^8$, and $R^9$ is —$NR^1R^2$, —OH, —SH, —$OR^1$, or —$SR^1$. In some cases, $R^1$ and $R^2$ are each independently substituted or unsubstituted alkyl, or $R^1$ and $R^2$ together with the nitrogen to which they are attached, form a substituted or unsubstituted 5- or 6-membered ring. Z may be a halogen, —SH, —$NHR^3$, —C(O)X, -maleimidyl, —$NHCOR^3$ or —$NHCO(CH_2)X$. $R^3$ can be hydrogen, substituted or unsubstituted alkyl, or an N-protecting group. X can be hydrogen, halogen, hydroxy, alkoxy, or O-succidimidyl; and n is 0, 1, 2, or 3. The compound may react with the peptide, for instance at a cysteine, aspartic acid, glutamic acid, or lysine residue.

Such a reaction may produce, in some embodiments, peptides having an amino acid residue of formula (XIII):

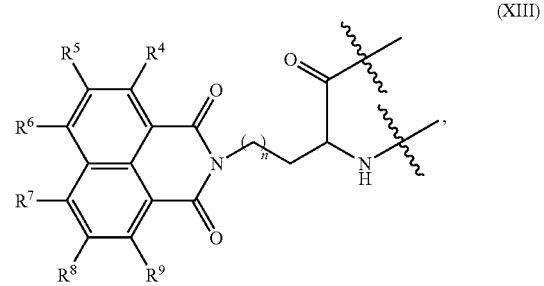

(XIII)

where n, $R^4$, $R^5$, $R^6$, $R^7$, $R^8$, and $R^9$ are as described above, or of formula (XIV),

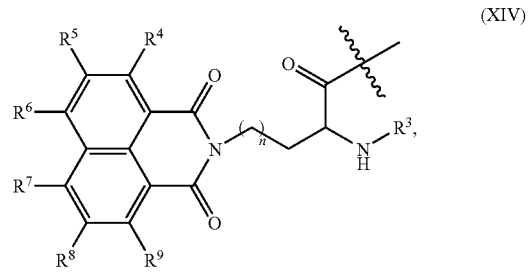

(XIV)

where $R^3$ is an N-protecting group, and n, $R^4$, $R^5$, $R^6$, $R^7$, $R^8$, and $R^9$ are as described above, or an amino acid residue of formula (XV):

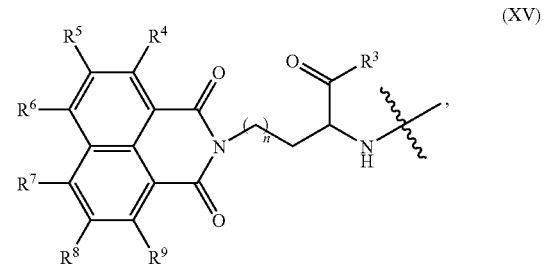

(XV)

wherein $R^3$ is a C-protecting group, and n, $R^4$, $R^5$, $R^6$, $R^7$, $R^8$, and $R^9$ are as described above. The amino acid residue can be present as the D-isomer or the L-isomer. Preferably, the amino acid residue is the D-isomer.

The peptide to be modified may be any suitable peptide, for example, naturally occurring, artificial or synthetically produced, etc. As a specific example, a peptide may be a peptide that comprises a target recognition sequence, such as an SH2-domain recognition sequence. Examples of SH2-domain recognition sequences include, but are not limited to, pTyr-Asp-His-Pro (SEQ ID NO: 11) or pTyr-Glu-Asn-Val (SEQ ID NO: 12).

Examples of synthesis techniques are discussed in the examples, below, and those of ordinary skill in the art will be able to readily modify such techniques as needed in order to reach a particular structure without an undue amount of experimentation. In some cases, a composition of the invention is synthesized using a commercially-available anhydride as a starting point.

Certain aspects of the present invention are generally directed to uses of the above-described compositions. For instance, in one set of embodiments, the compositions are useful as fluorescence probe molecules in applications wherein fluorescence probes are known to be useful. A composition of the present invention can be added to a sample to be probed. The sample comprising the composition was then exposed to a light source. The light source produces light that may have a range of wavelengths. As examples, the wavelengths may be (but are not limited to) between about 320 and about 530 nanometers (nm), between about 380 and about 490 nm, or between about 440 and about 445 nm. In some cases, the emitted fluorescent energy may have a range of wavelengths between about 410 and about 630 nm, or between about 490 and about 542 nm, among other ranges.

Upon exposure to a light source, a composition of the present invention, which is fluorescent, may emit fluorescent energy. The emitted fluorescent energy can be detected using methods well known in the art. In some cases, the intensity and/or wavelength of the emitted fluorescent energy provides information about the sample.

The fluorescence of a molecule may be defined by the quantum yield. The quantum yield is the ratio of the photons absorbed by the compound to the photons emitted through fluorescence by the compound. Compounds of the present invention have quantum yields that may be relatively low in aqueous solutions, but higher in non-polar environments. Quantum yields for various embodiments may range from about 0.001 and about 0.1, or between about 0.001 and about 0.005 for aqueous solutions, or between about 0.2 and about 0.7 for non-polar environment.

The fluorescence can also be evaluated by determining the dipole moment change between the ground and excited state. The change in the dipole moment can be estimated from a plot of the Stokes shift vs. the orientation polarizability, known as a Lippert-Mataga plot, known to those of ordinary skill in the art. As fluorescence can be sensitive to the pH of the surrounding environment, certain compositions of the present invention are useful as fluorescence probes or sensors in the pH range from about 4 to about 8.

In another set of embodiments, the compositions of the present invention may be useful in monitoring biological interactions. Biological interactions play important roles in the sequence and mechanisms of action of various cellular processes and signal pathways. Accordingly, the time course, nature, and sequence of the different cellular processes can be elucidated by in situ observation using certain compositions of the present invention. Specific inhibitors and/or activators of the cellular processes and signal pathways may optionally be used in addition to compounds of the present invention.

Biological interactions, as defined herein, comprise the interaction of a compound or molecule with a target molecule. Examples of target molecules include peptides, proteins, enzymes, nucleic acids, ions, and other receptors; metal ion chelators, proteases, polymerases, hydrolases, phosphatases, and kinases; protein domains, and protein domains of phosphatases and kinases.

Proteins and protein-protein interactions play a central role in the various biochemical processes. For example, these interactions are evident in the interaction of hormones with their respective receptors, in the intracellular and extracellular signaling events mediated by proteins, in enzyme substrate interactions, in intracellular protein trafficking, in the formation of complex structures like ribosomes, viral coat proteins, and filaments, or in antigen-antibody interactions. These interactions are usually facilitated by the interaction of small regions within the proteins that can fold independently of the rest of the protein. These independent units are called protein domains. Abnormal or disease states can be the direct result of aberrant protein-protein interactions. Protein-protein interactions are also central to the mechanism of a virus recognizing its receptor on the cell surface as a prelude to infection. Identification of domains that interact with each other not only leads to a broader understanding of protein-protein interactions, but also aids in the design of inhibitors of these interactions.

Phosphorylation-dependent peptide-protein interactions include phosphoserine peptides with 14-3-3, which is a protein involved in cell cycle control, and phosphotyrosine peptides with SH2 domains. SH2 domains are binding modules that are involved in tyrosine kinase signaling networks and recognize phosphotyrosine-containing peptide sequences. The phosphotyrosine binding is complemented by simultaneous peptide-protein interactions on the protein surface. Examples of SH2 domains include Abl SH2, Crk SH2, and C-terminal P13K SH2 which can be expressed in bacteria as GST fusion proteins, which are referred to as GST-Abl SH2, GST-Crk SH2, and GST-PI3K SH2.

The recognition sequences for SH2 domains may comprise phosphotyrosine residues and other amino acids. The recognition sequence is different for different SH2 domains. Amino acid recognition sequences for binding members of the SH2 domain family are disclosed. For the Crk SH2 domain, the recognition sequence is pTyr-Asp-His-Pro (SEQ ID NO: 11). For the Abl SH2 domain, the recognition sequence is pTyr-Glu-Asn-Val (SEQ ID NO: 12).

The compositions of formula (I), and of any other formulae described herein, may be useful for studying the peptide-protein interactions on the protein surface of the SH2 domain, according to one set of embodiments. Here, compositions of formula (I) can be incorporated into peptides containing the desired SH2 recognition sequence. Table 1 shows peptides incorporating the Crk SH2 or Abl SH2 recognition sequences and Dap(4-DMN) into the (+2) position relative to the phosphotyrosine residue. In addition, the peptides of Table 1 can be incubated with targeted and nontargeted SH2 domains. The binding of peptides Crk-bp, Crk-bp2, Abl-bp, and Abl-bp2 to SH2 target domains can be studied by fluorescence titration.

TABLE 1

| Peptide | Target SH2 | Peptide sequence |
|---|---|---|
| Crk-bp | Crk | Ac-Glu-Dap(4-DMN)-Gln-pTyr-Asp-His-Pro-Asn-Ile-(CONH$_2$) (SEQ ID NO: 1) |
| Crk-bp2 | Crk | Ac-Glu-Dap(4-DMN)-Gly-pTyr-Asp-His-Pro-Asn-Ile-(CONH$_2$) (SEQ ID NO: 2) |
| Abl-bp | Abl | Ac-Glu-Dap(4-DMN)-Gly-pTyr-Glu-Asn-Val-Gln-Ser-(CONH$_2$) (SEQ ID NO: 3) |
| Abl-bp2 | Abl | Ac-Glu-Dap(4-DMN)-pTyr-Glu-Asn-Val-Gln-Ser-(CONH$_2$) (SEQ ID NO: 4) |

The compositions are also useful in various aspects of the present invention generally directed to biological interactions and methods of monitoring biological interactions.

In some embodiments, the method includes providing a composition, contacting a target molecule with the composition to form a biological sample, and determining the fluorescence of the biological sample. The target molecule may be a peptide. For instance, the compound may be a peptide containing at least one of formulae (II) and (VI). As another example, the compound may be a peptide containing an amino acid residue that is modified by at least one of formulae (VII), (IX), or (XI).

In certain of the methods of the present invention, the monitoring step comprise contacting a composition with the one or more target molecules or different biochemical conditions, wherein the measuring step comprises exciting the composition with light, and measuring the fluorescence.

In some of the methods of using a composition of the present invention, the concentration used may depend on external factors such as the detection equipment. Typically, the concentration of the composition in the sample is from greater than about 0.1 nM. A sensor of various embodiments of the present invention can be used in a method for detecting biological interactions. The methods of certain embodiments of the present invention include providing a peptide incorporating an amino acid of formula (II), contacting a target molecule with the peptide to form a biological sample, and monitoring the fluorescence of the biological sample. In another embodiment, the method of the present invention comprises providing a peptide comprising an amino acid residue that is modified by a compound of formula (VII), contacting a target molecule with the peptide to form a biological sample, and monitoring the fluorescence of the biological sample.

When describing the compounds, compositions, methods and processes of this invention, the following terms have the following meanings, unless otherwise indicated. Following, and interspersed with these definitions, is further disclosure that will more fully describe the invention.

The term "hydroxy" means the —OH group.

The term "amino" means the —NR'R" group, where R' and R" are each independently hydrogen or alkyl.

The term "thiol" means the —SR' group, where R' is hydrogen.

The term "halogen" or "halo" means a chlorine, bromine, iodine, or fluorine atom.

The term "alkyl" means a hydrocarbon group that may be linear, cyclic, or branched or a combination thereof having the number of carbon atoms designated (i.e., C1-8 means one to eight carbon atoms). Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl, bicyclo[2.2.1]heptane, bicyclo[2.2.2]octane, etc. Alkyl groups can be substituted or unsubstituted, unless otherwise indicated. Examples of substituted alkyl groups include haloalkyl, thioalkyl, aminoalkyl, and the like.

The term "aryl" means a polyunsaturated, aromatic hydrocarbon group having a single ring (monocyclic) or multiple rings (bicyclic or polycyclic), which can be fused together or linked covalently. Examples of aryl groups include phenyl and naphthalene-1-yl, naphthalene-2-yl, biphenyl and the like. Aryl groups can be substituted or unsubstituted, unless otherwise indicated.

The term "heteroaryl" means an aromatic group containing at least one heteroatom, where the heteroaryl group may be monocyclic or bicyclic. Examples include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl.

The term "heterocyclyl" or "heterocyclic," which are synonymous as used herein, means a saturated or unsaturated ring containing at least one heteroatom (typically 1 to 5 heteroatoms) selected from nitrogen, oxygen or sulfur. The heterocyclyl ring may be monocyclic or bicyclic. Examples of heterocycle groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like.

The term "ring" means a compound whose atoms are arranged in formulas in a cyclic form. The ring compound can be either carbocyclic or heterocyclic.

The term "carbocyclic" means a ring composed exclusively of carbon atoms.

The term "substituent" means an atom or a group that replaces another atom or group in a molecule.

The terms "N-terminal protecting group" or "N-protecting group" refer to a group that prevents undesirable reaction of the amino functional group during subsequent transformations. The use of N-protecting groups is well known in the art for protecting groups against undesirable reactions during a synthetic procedure and many such protecting groups are known. Commonly used N-protecting groups are known to those skilled in the art, examples of which are disclosed in Greene and Wuts, Protective Groups in Organic Synthesis, 2nd ed.; John Wiley & Sons, New York, 1991). Examples of N-protecting groups include, but are not limited to, benzyl, substituted benzyl, benzyloxycarbonyl (Cbz), tert-butoxycarbonyl (Boc), 9-fluorenylmethoxycarbonyl (Fmoc), trityl, N-veratyloxycarbonyl (N-Voc), N-allyloxycarbonyl (N-Alloc) and N-pentenoyl (N-Pent), acyl groups including formyl, acetyl (Ac), trifluoroacetyl, trichloroacetyl, propionyl, pivaloyl, t-butylacetyl, acylisothiocyanate, aminocaproyl, benzoyl and the like; acyloxy groups, including t-butyloxycarbonyl (Boc), benzyloxycarbonyl (Cbz), 9-fluorenylmethoxycarbonyl (Fmoc), p-methoxybenzyloxycarbonyl, methoxycarbonyl, ethoxycarbonyl, allyloxycarbonyl and the like; sulfonyl groups such as benzenesulfonyl, p-toluenesulfonyl and the like; arylalkyl groups such as benzyl, triphenylmethyl, benzyloxymethyl and the like; and silyl groups such as trimethylsilyl, t-butyldimethylsilyl and the like.

The term "C-terminal protecting group" refers to a group that prevents undesirable reaction of the carboxyl functional group and includes, but is not limited to, $C_1$-$C_{12}$ alkyl (e.g., tert-butyl) and $C_1$-$C_{12}$ haloalkyl.

The term "chelation-enhanced fluorescence (CHEF)" means fluorescence enhancement of a compound as a result of metal ion binding (chelation) to that compound.

The term "capping group" means a chemical group connected to the N- or C-terminus of a peptide to prevent the peptide from degrading.

"Alkoxy" refers to —O-alkyl. Examples of an alkoxy group include methoxy, ethoxy, n-propoxy, etc.

"Haloalkyl," as a substituted alkyl group, refers to a monohaloalkyl or polyhaloalkyl group, most typically substituted with from 1-3 halogen atoms. Examples include 1-chloroethyl, 3-bromopropyl, trifluoromethyl and the like.

All of the above terms (e.g., "alkyl," "aryl," "heteroaryl" etc.), in some embodiments, include both substituted and unsubstituted forms of the indicated groups. These groups may be substituted multiple times, as chemically allowed. Suitable substituents include alkyl, aryl, heteroaryl, heterocyclyl, halogen, alkoxy, oxygen, and nitrogen.

Certain compounds of the present invention can exist in unsolvated forms as well as solvated forms, including hydrated forms. In general, both solvated forms and unsolvated forms are intended to be encompassed within the scope of the present invention. Certain compounds of the present invention may exist in multiple crystalline or amorphous forms (i.e., as polymorphs). In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

"Fluorescence" encompasses the release of fluorescent energy. Less broadly, the term "fluorescence" refers to fluorescent emission, the rate of change of fluorescence over time (i.e., fluorescence lifetime), fluorescence polarization, fluorescence anisotropy, and fluorescence resonance energy transfer. See Eftink, M. R., Biophysical J. 66:482-501 (1994).

"Fluorescence probe molecule" refers to a compound of the present invention. The compound, after excitement by light of a defined wavelength or defined range of wavelengths, is capable of emitting fluorescent energy. The fluorescent molecule or a compound may be capable of binding to a peptide, protein, membrane or receptor.

The term "biological interactions" encompasses the interaction of a compound or molecule with a target molecule.

"Protein" and "peptide," as used herein, are synonymous. The peptide may comprise any number of amino acids. For instance, the peptide of the present invention may comprise 2-100 amino acids, 2-30 amino acids, 2-20 amino acids, or 3-10 amino acids. For proteins or peptides, the term "unfolding" encompasses any change in structure due to heating. For example, the term "unfolding" refers to the transition of from the liquid crystalline state to the molten globule state. In the molten globule state, tertiary and quaternary structure has been altered, relative to the native state of the protein, and at least some secondary structure remains intact. The term "unfolding" also encompasses loss of crystalline ordering of amino acid side-chains, secondary, tertiary or quaternary structure. The term "unfolding" also encompasses formation of a random coil.

"Folding" and "refolding," and "renaturing" refer to the acquisition of the correct amino acid side-chain ordering, secondary, tertiary, or quaternary structure, of a protein or a nucleic acid, which affords the full chemical and biological function of the biomolecule.

The term "target molecule" encompasses peptides, proteins, nucleic acids, ions, and other receptors. The term encompasses both enzymes, and proteins which are not enzymes. The term encompasses monomeric and multimeric proteins. Multimeric proteins may be homomeric or heteromeric. The term encompasses nucleic acids comprising at least two nucleotides, such as oligonucleotides. Nucleic acids can be single-stranded, double-stranded, or triple-stranded. The term encompasses a nucleic acid which is a synthetic oligonucleotide, a portion of a recombinant DNA molecule, or a portion of chromosomal DNA. The term target molecule also encompasses portions of peptides, proteins, and other receptors which are capable of acquiring secondary, tertiary, or quaternary structure through folding, coiling or twisting. The target molecule may be substituted with substituents including, but not limited to, cofactors, coenzymes, prosthetic groups, lipids, oligosaccharides, or phosphate groups.

The terms "target molecule" and "receptor" are synonymous. Examples of target molecules are included, but not limited to those disclosed in Faisst, S. et al., Nucleic Acids Research 20:3-26 (1992); Pimentel, E., Handbook of Growth Factors, Volumes I-III, CRC Press, (1994); Gilman, A. G. et al., The Pharmacological Basis of Therapeutics, Pergamon Press (1990); Lewin, B., Genes V, Oxford University Press (1994); Roitt, I., Essential Immunology, Blackwell Scientific Publ. (1994); Shimizu, Y., Lymphocyte Adhesion Molecules, R G Landes (1993); Hyams, J. S. et al., Microtubules, Wiley-Liss (1995); Montreuil, J. et al., Glycoproteins, Elsevier (1995); Woolley, P., Lipases: Their Structure Biochemistry and Applications, Cambridge University Press (1994); Kurjan, J., Signal Transduction Prokaryotic and Simple Eukaryotic Systems, Academic Press (1993); Kreis, T., et al., Guide Book to the Extra Cellular Matrix and Adhesion Proteins, Oxford University Press (1993); Schlesinger, M. J., Lipid Modifications of Proteins, CRC Press (1992); Conn, P. M., Receptors: Model Systems and Specific Receptors, Oxford University Press (1993); Lauffenberger, D. A. et al, Receptors. Models For Binding Trafficking and Signaling, Oxford University Press (1993); Webb, E. C., Enzyme Nomenclature, Academic Press (1992); Parker, M. G., Nuclear Hormone Receptors; Molecular Mechanisms, Cellular Functions Clinical Abnormalities, Academic Press Ltd. (1991); Woodgett, J. R., Protein Kinases, Oxford University Press (1995); Balch, W. E. et al., Methods in Enzymology, Vol. 257, Pt. C: "Small GTPases and Their Regulators: Proteins Involved in Transport," Academic Press (1995); The Chaperonins, Academic Press (1996); Pelech, L., Protein Kinase Circuitry in Cell Cycle Control, R G Landes (1996); Atkinson, Regulatory Proteins of the Complement System, Franklin Press (1992); Cooke, D. T. et al., Transport and Receptor Proteins of Plant Membranes: Molecular Structure and Function, Plenum Press (1992); Schumaker, V. N., Advances in Protein Chemistry: Lipoproteins, Apolipoproteins, and Lipases, Academic Press (1994); Brann, M., Molecular Biology of G-Protein-Coupled Receptors: Applications of Molecular Genetics to Pharmacology, Birkhauser (1992); Konig, W., Peptide and Protein Hormones: Structure, Regulations, Activity—A Reference Manual, VCH Publ. (1992); Tuboi, S. et al., Post-Translational Modification of Proteins, CRC Press (1992); Heilmeyer, L. M., Cellular Regulation by Protein Phosphorylation, Springer-Verlag (1991); Takada, Y., Integrin: The Biological Problem, CRC Press (1994); Ludlow, J. W., Tumor Suppressors Involvement in Human Disease, Viral Protein Interactions, and Growth Regulation, R G Landes (1994); Schlesinger, M. J., Lipid Modification of Proteins, CRC Press (1992); Nitsch, R. M., Alzheimer's Disease. Amyloid Precursor Proteins, Signal Transduction, and Neuronal Transplantation, New York Academy of Sciences (1993); Cochrane, C. G., et al., Cellular and Molecular Mechanisms of Inflammation, Vol. 3: Signal Transduction in Inflammatory Cells, Part A, Academic Press (1992); Gupta, S. et al., Mechanisms of Lymphocyte Activation and Immune Regulation IV: Cellular Communications, Plenum Press (1992); Authi, K. S. et al., Mechanisms of Platelet Activation and Control, Plenum Press (1994); Grunicke, H., Signal Transduction Mechanisms in Cancer, R G Landes (1995); Latchman, D. S., Eukaryotic Transcription Factors, Academic Press (1995).

The term "contacting a target molecule" refers broadly to placing the target molecule in solution with the molecule to be screened for binding or with the condition(s) to be tested for stabilizing the target molecule. Less broadly, contacting refers to the turning, swirling, shaking or vibrating of a solution of the target molecule and the molecule to be screened for binding. More specifically, contacting refers to the mixing of the target molecule with the molecule to be tested for binding. Mixing can be accomplished, for example, by repeated uptake and discharge through a pipette tip, either manually or using an automated pipetting device. Contacting can refer to the equilibration of binding between the target molecule and the molecule to be tested for binding. Contacting can occur in the container, infra, or before the target molecule and the molecule to be screened are placed in the container.

The target molecule may be contacted with a nucleic acid prior to being contacted with the molecule to be screened for binding. The target molecule may be complexed with a peptide prior to being contacted with the molecule to be screened for binding. The target molecule may be phosphorylated or dephosphorylated prior to being contacted with the molecule to be screened for binding.

A carbohydrate moiety may be added to the target molecule before the target molecule is contacted with the molecule to be screened for binding. Alternatively, a carbohydrate moiety may be removed from the target molecule before the target molecule is contacted with the molecule to be screened for binding.

The term "container" refers to any vessel or chamber in which the receptor and molecule to be tested for binding can be placed. The term "container" encompasses reaction tubes (e.g., test tubes, microtubes, vials, etc.).

"Spectral emission," "thermal change," and "physical change" encompass the release of energy in the form of light or heat, the absorption of energy in the form or light or heat, changes in turbidity and changes in the polar properties of light. Specifically, the terms refer to fluorescent emission, fluorescent energy transfer, absorption of ultraviolet or visible light, changes in the polarization properties of light, changes in the polarization properties of fluorescent emission, changes in the rate of change of fluorescence over time (i.e., fluorescence lifetime), changes in fluorescence anisotropy, changes in fluorescence resonance energy transfer, changes in turbidity, and changes in enzyme activity. The terms may refer to fluorescence, including to fluorescence emission. Fluorescence emission can be intrinsic to a protein or can be due to a fluorescence reporter molecule. The use of fluorescence techniques to monitor protein unfolding is well known to those of ordinary skill in the art. For example, see Eftink, M. R., Biophysical J. 66:482-501 (1994).

"Biochemical conditions" encompass any component of a physical, chemical, or biochemical reaction. Specifically, the term refers to conditions of temperature, pressure, protein concentration, pH, ionic strength, salt concentration, time, electric current, potential difference, concentrations of cofactor, coenzyme, oxidizing agents, reducing agents, detergents, metal ion, ligands, or glycerol.

As used herein, the term "determining" generally refers to the analysis of a species, for example, quantitatively or qualitatively, and/or the detection of the presence or absence of the species. "Determining" may also refer to the analysis of an interaction between two or more species, for example, quantitatively or qualitatively, and/or by detecting the presence or absence of the interaction.

U.S. patent application Ser. No. 11/710,789, filed Feb. 26, 2007, entitled "Environmentally Sensitive Fluorophores," by B. Imperiali, et al., is incorporated herein by reference.

The following examples are intended to illustrate certain embodiments of the present invention, but do not exemplify the full scope of the invention.

EXAMPLE 1

This example illustrates the synthesis of 4-DMN, which is similar to that of 6-DMN. See, for example, the synthesis method set forth in U.S. patent application Ser. No. 11/106,349, filed Apr. 13, 2005, entitled "Fluorescent Probes for Biological Studies," by B. Imperiali, et al., published as U.S. Patent Application Publication No. 2006/0234206 on Oct. 19, 2006, the entirety of which is herein incorporated by reference.

Figure 1C:
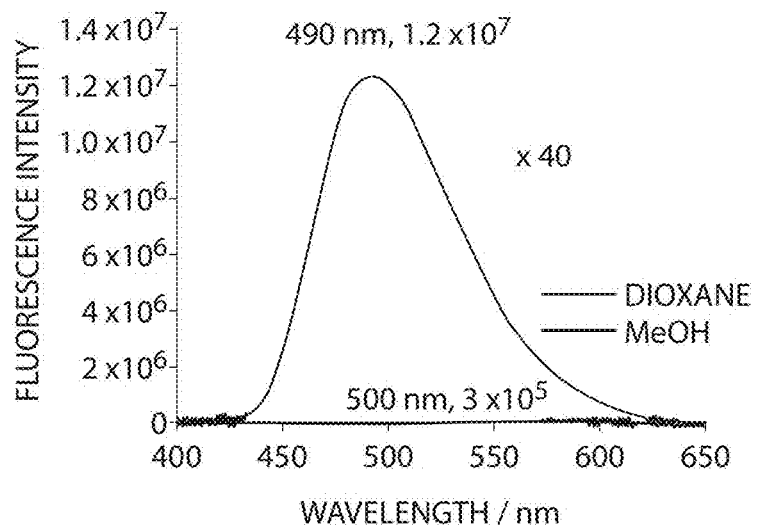
Figure 1D:
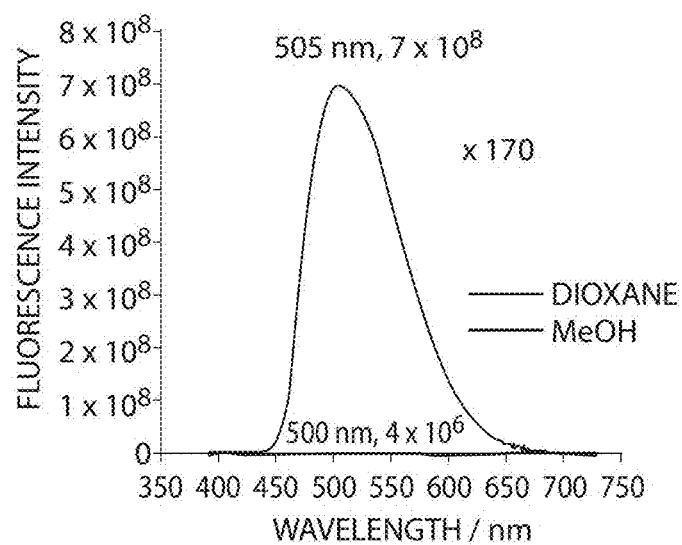

FIG. 1 illustrates the structures of the Dap(6-DMN) (FIG. 1A) and Dap(4-DMN) (FIG. 1B), the fluorescence excitation and emission maxima, and the changes in fluorescence spectra in methanol and dioxane for the two compounds (FIGS. 1C and 1D, respectively). The latter are indicative of the large changes that can be achieved for signaling protein/protein and peptide/protein interactions when the 4-DMN group is integrated to one of the binding partners either as an amino acid (e.g. 22) or via chemical modification of a cysteine in one of the sequences. The fluorophore is incorporated into the amino acid (22) for integration into peptides by solid-phase peptide synthesis or into proteins by protein semi-synthesis.

The synthesis of the peptides was as follows. Referring to FIG. 2, the fluorophore was incorporated into compounds, such as 23 and 24, that could be used for the selective chemical modification of cysteine in intact peptides and proteins. The sensor peptides were synthesized in this example via standard solid-phase peptide synthesis.

The peptide synthesis was carried out using standard Fmoc-based solid phase peptide synthesis (SPPS) protocols on a 0.05 to 0.1 mmol scale using a 0.21 mmol/g loading PAL-PEG-PS solid support. Amino acids were coupled in three-fold excess using a mixture of 0.2 M HBTU/0.2 M HOBt in DMF as activating agents. Each amino acid was activated for two minutes with the HBTU/HOBt mixture (1 eq.) and diisopropylethylamine (DIPEA), 0.195 M in DMF (1.5 eq.) before being added to the resin. Peptide coupling was monitored using the 2,4,6-trinitrobenzenesulphonic acid (TNBS) test. Amino acids were used as protected Fmoc-amino acids with the standard side chain protecting groups. High-performance liquid chromatography (HPLC) was performed using a Waters 600E HPLC fitted with a Waters 600 automated control module and a Waters 2487 dual wavelength absorbance detector recording at 228 and 280 nm. For analytical HPLC, a Beckman Ultrasphere C18, 5 micrometer, 4.6×150 mm reverse-phase column was used. For preparative separations, a YMC-pack, C18, 250×20 mm reversed phase column was used. The standard gradient for analytical and preparative HPLC used was 93:7 to 5:95 over 35 minutes (water:acetonitrile, 0.1% TFA). The 4DMN side chain proved resistant to the standard mildly basic amino acid coupling conditions (0.12 M diisopropylethylamine), the Fmoc deprotection conditions (20% piperidine), and the acidic resin cleavage and deprotection cocktail (95% TFA).

The methods for quantum yields measurement, Lippert-Mataga plots, fluorescence titrations and determination of binding constant (Kd), expression of GST-Crk SH2, western blot, expression of GST-AbI SH2, GST-Src SH2 and GST-PI3K SH2 were similar to the methods set forth in U.S. Patent Application Publication No. 2006/0234206 (referenced above), incorporated herein by reference.

EXAMPLE 2

Figure 3A:
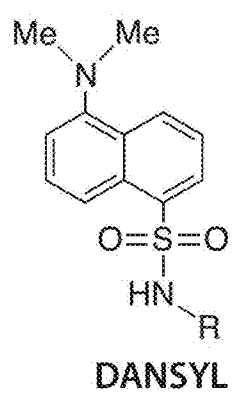
FIGS. 3A-3E illustrate various fluorescent compounds.
Figure 3B:
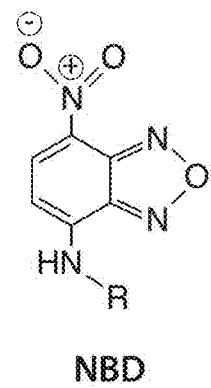

Since their introduction, derivatives of the 7-nitrobenz-2-oxa-1,3-diazole (NBD) and dansyl fluorophores (FIGS. 3A-3B) have been used extensively in the areas of cell biology and protein biochemistry. Both exhibit high fluorescence quantum yields in hydrophobic environments compared to the lower fluorescence yields observed in hydrophilic environments such as buffered water. This permits the possibility to probe the dynamics of many biological macromolecules that can undergo dramatic allosteric changes in tertiary structure or participate in highly regulated interactions with other macromolecules. Such processes can often result in the creation or elimination of hydrophobic microenvironments, which may readily be detected by a strategically placed environment sensitive fluorophore. However, both of these fluorophores possess characteristics that limit their application in the field of fluorescence microscopy. For instance, the wavelength of maximum excitation of dansyl is below 350 nm where background autofluorescence can interfere with signal measurements (Table 2). The NBD group excites at much longer wavelengths, but exhibits a significant amount of fluorescence in water compared to dansyl resulting in a much smaller change in fluorescence when introduced to a hydrophobic environment. NBD also gives a much smaller hypsochromic shift in its emission spectrum than dansyl.

intensity in dioxane. This contrast to both dansyl and NBD is due to the exceptionally low background fluorescence exhibited by these fluorophores in aqueous environments (FIG. 5A-5E). An advantage of this property is a much improved signal-to-noise ratio for experimental measurements made in the context of real biological systems. In application, environment sensitive fluorophores rarely yield their maximum fluorescence potential as seen in hydrophobic solvents like dioxane. While it is often possible to optimize the maximum fluorescence output by experimenting with the placement of the selected fluorophore on the protein of interest, the intrinsic fluorescence of the fluorophore in aqueous environments is often a limiting factor when optimizing the fluorescent response.

EXAMPLE 3

Figure 6A:
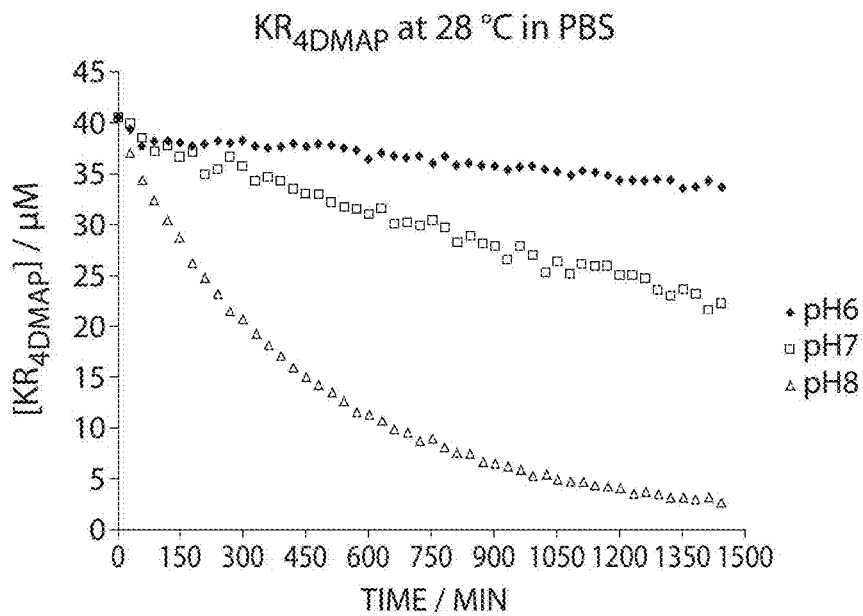
FIGS. 6A-6B illustrate hydrolysis of a compound of the invention, in one embodiment.
Figure 6B:
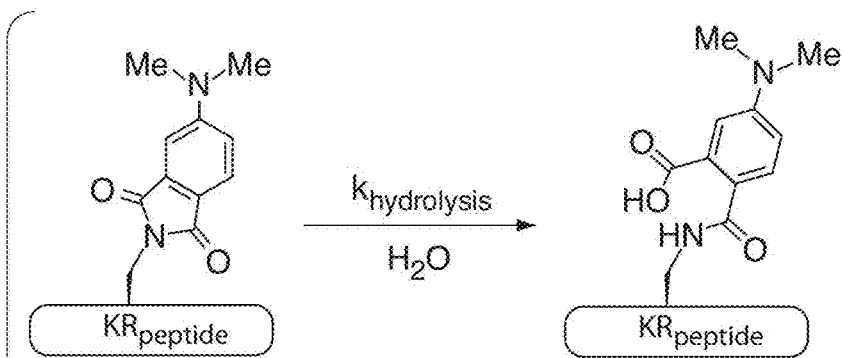

The 4DMAP and 6DMN fluorophores are likely susceptible to the gradual hydrolysis of the imide ring system in the pH range of 7 to 8. The origin of this reactivity can be attributed to the bond angle strain of the five-membered imide ring system that is released during the ring opening process. By comparison, the 4DMN fluorophore, which possesses a six-membered imide ring system, exhibited no such reactivity. This is apparent in an experiment performed on both the $KR_{4DMAP}$ and $KR_{4DMN}$ peptides using a PerkinElmer HTS7000 plate reader. Fluorescence of the two peptides was measured at their respective emission wavelengths in PBS buffer over a 24 hour period at 28° C. The 4DMAP fluorophore did not appear to be fluorescent in the hydrolyzed state allowing its degradation to be quantified over time. As shown in FIGS. 6A-6B, the rate of hydrolysis appeared to be significantly enhanced at pH 8.

TABLE 2

Results of comparative study of the KR peptide series in dioxane vs. TBS buffer

| Fluorophore | $\lambda_{abs}$ (nm) | $\epsilon(M^{-3} cm^{-3})$ | $\lambda_{exc}$ (nm) | $\lambda_{em}$ (nm) TBS | $\lambda_{em}$ (nm) dioxane | $I_{dioxane}/I_{TBS}$ @ $\lambda_{em}$ in dioxane* |
|---|---|---|---|---|---|---|
| $KR_{4DMAP}$ | 421 | $6.5 \times 10^3$ | 390 | 580 | 497 | $4.5 \times 10^3 \pm 1.4 \times 10^3$ |
| $KR_{4DMN}$ | 440 | $8.8 \times 10^3$ | 408 | 554 | 512 | $1.2 \times 10^3 \pm 0.2 \times 10^3$ |
| $KR_{6DMN}$ | 390 | $8.0 \times 10^3$ | 378 | 625 | 520 | $1.4 \times 10^3 \pm 0.2 \times 10^3$ |
| $KR_{dansyl}$ | 337 | $5.3 \times 10^3$ | 345 | 564 | 499 | $66 \pm 1$ |
| $KR_{NBD}$ | 465 | $2.2 \times 10^4$ | 455 | 543 | 523 | $7.0 \pm 0.3$ |

*The listed errors represent the 90% confidence interval from an average of three trials.

Figure 3C:
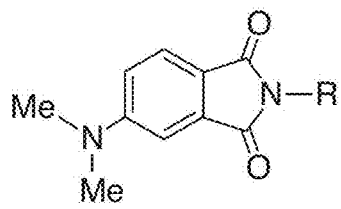
Figure 3D:
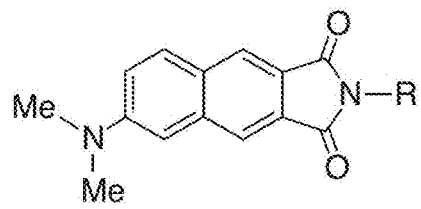
Figure 3E:
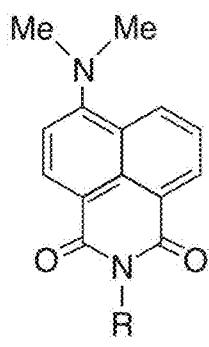
Figure 4:
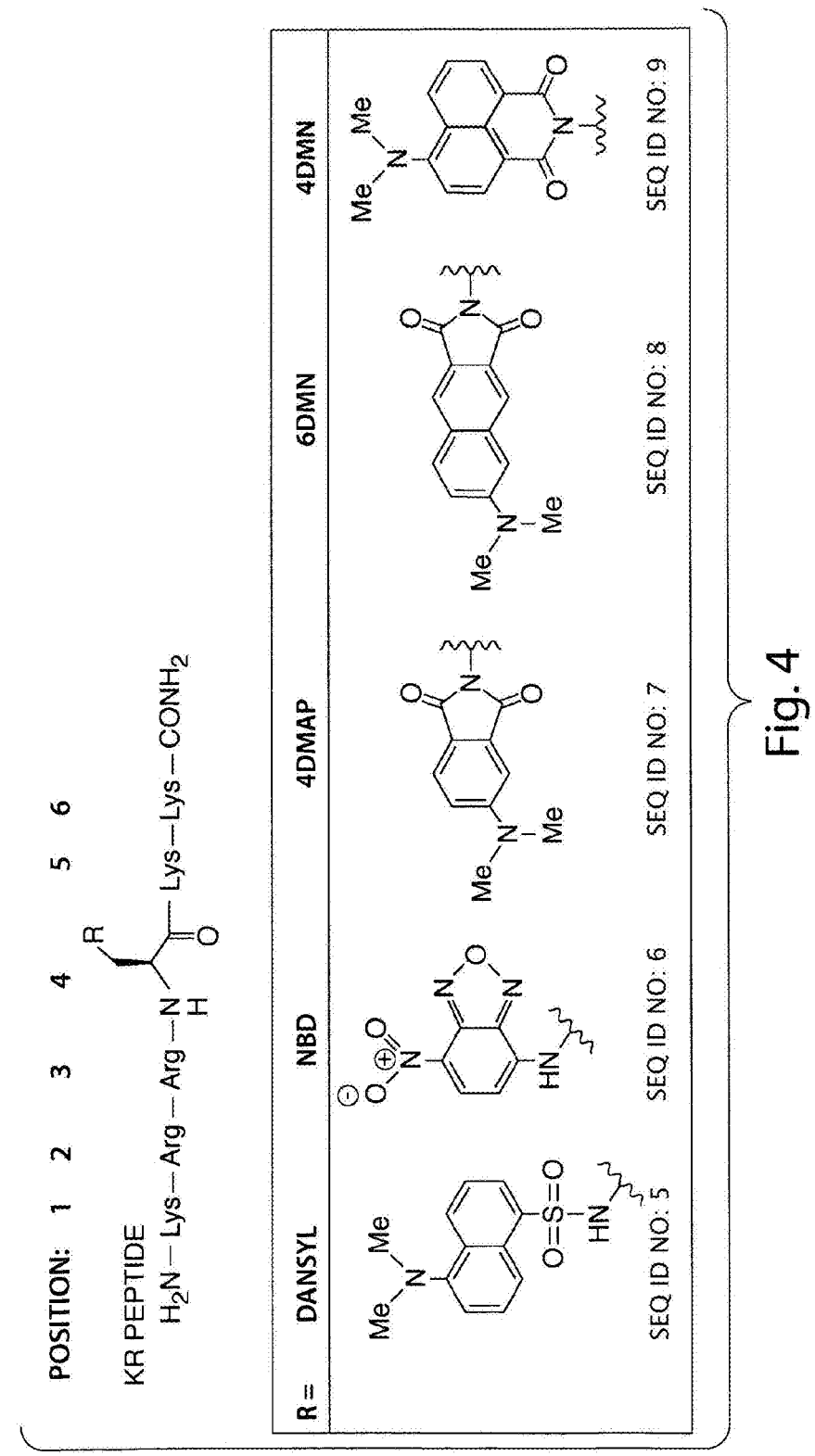
FIG. 4 illustrates peptides that include various fluorescent compounds.
Figure 5A:
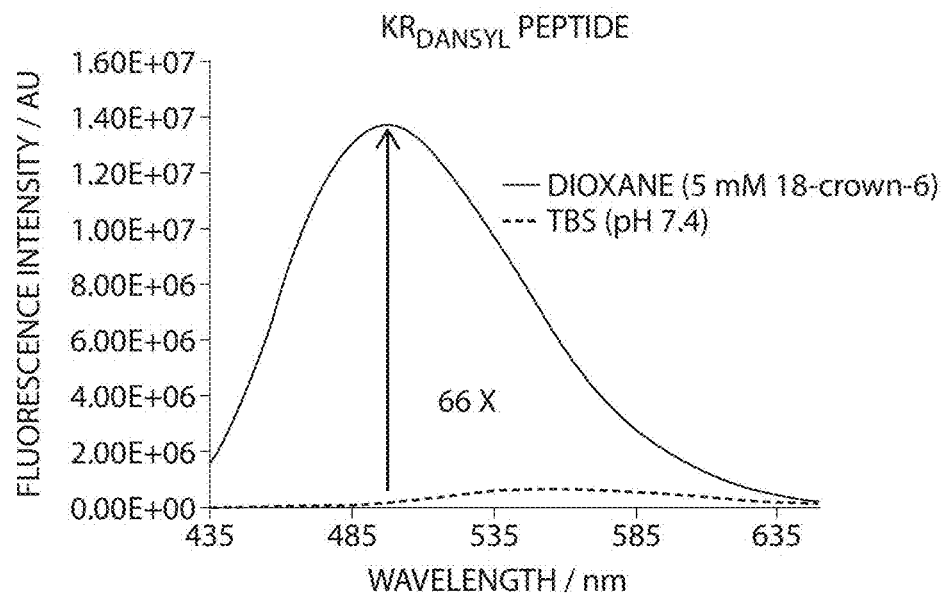
FIGS. 5A-5E illustrate various fluorescent spectra of certain compounds.
Figure 5B:
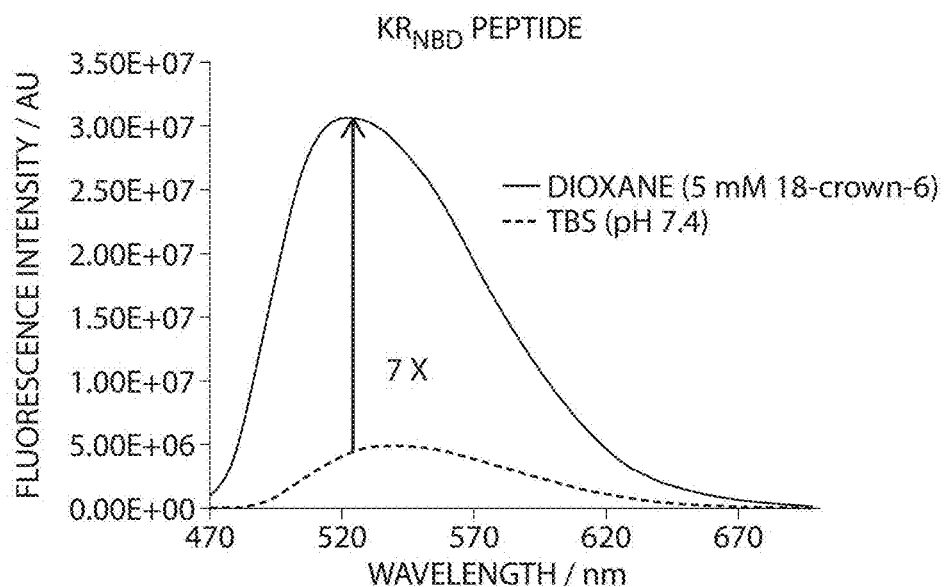
Figure 5C:
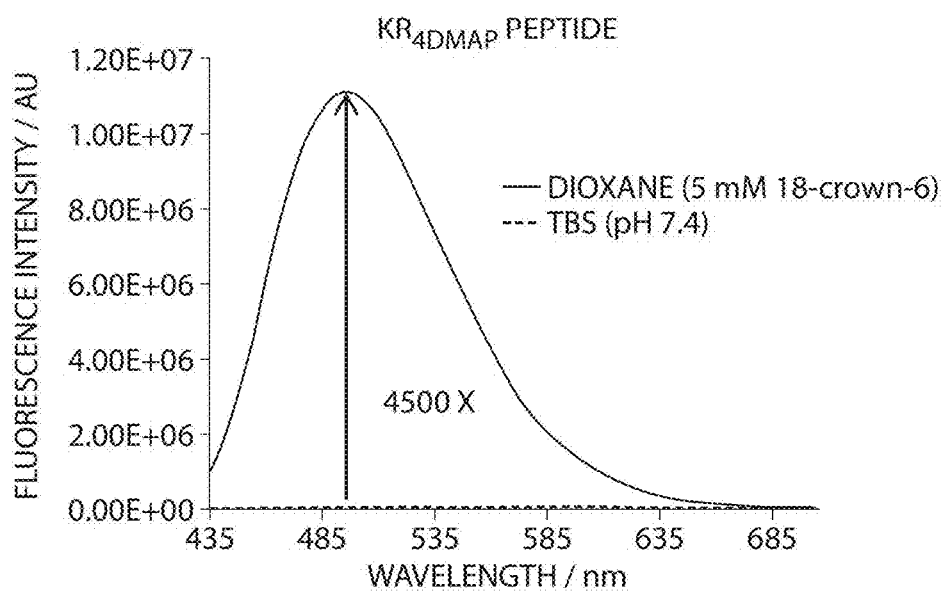
Figure 5D:
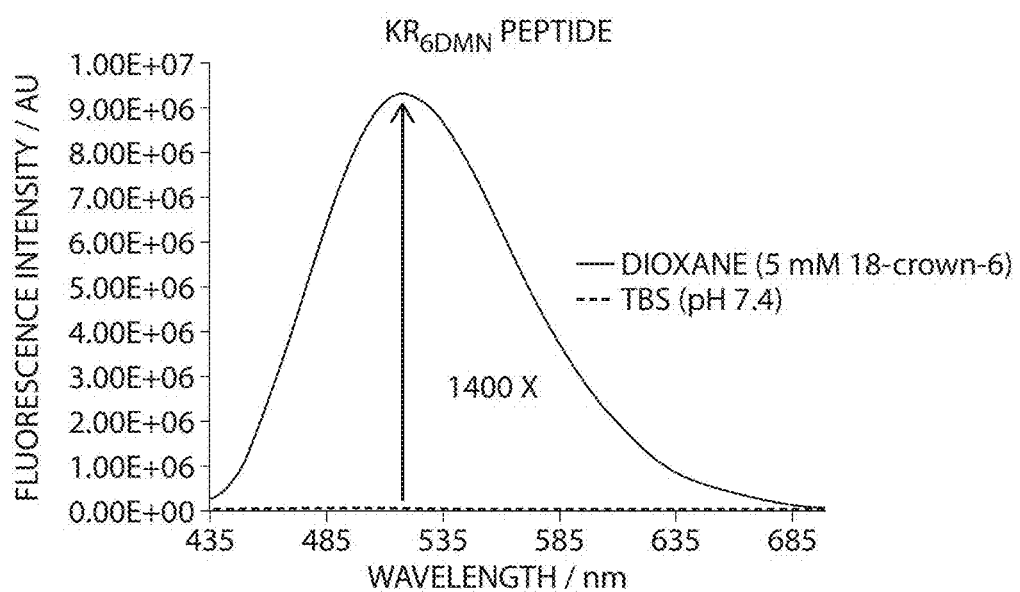
Figure 5E:
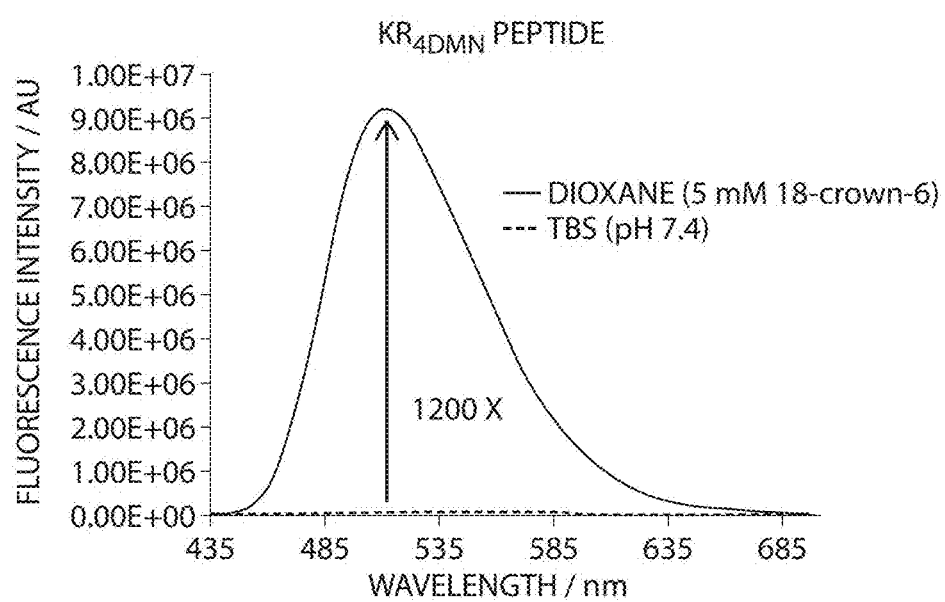
Figure 7:
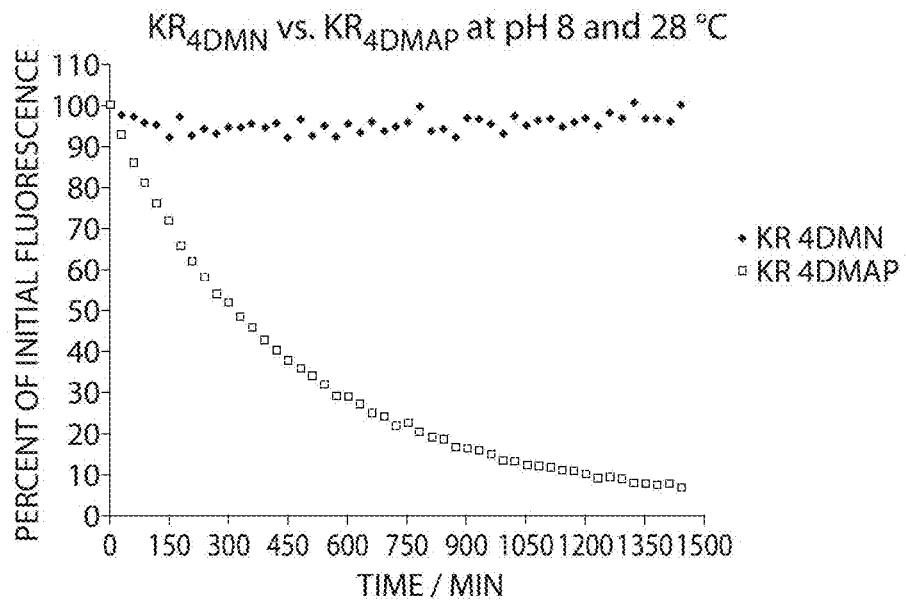
FIG. 7 illustrates hydrolysis of a compound of the invention, in another embodiment.

This example illustrates investigations into the biological applications of the dimethylamino phthalimide series of environment sensitive fluorophores (FIGS. 3C-3E), as compared to both dansyl and NBD. A comparative study was performed on the fluorophores of FIG. 3 by synthetically preparing a series of lysine-arginine rich peptides (KR peptide series) such that each peptide in the series contained one of the five fluorophores appended to the side-chain of the residue at position 4 in the peptide sequence (FIG. 4), SEQ ID NOs: 5-9. The fluorescence spectra of the KR peptides were then measured at 5 micromolar in both TBS buffer (pH 7.4) and dioxane (containing 5 mM 18-crown-6). These conditions were selected to determine the magnitude of the fluorescence change for each fluorophore under an ideal set of conditions. The fluorophores that possessed the greatest ratio of fluorescence in dioxane over that in TBS buffer were those of the dimethylamino phthalimide series (Table 1). The 4-dimethylamino phthalimide (4DMAP), 6-N,N-dimethylamino-2,3-naphthalimide (6DMN), and 4-N,N-dimethylamino-1,8-naphthalimide (4DMN) fluorophores each exhibited fluorescence intensity ratios ($I_{dioxane}/I_{TBS}$) greater than three orders of magnitude at the wavelength of maximum emission When the same study was performed on the $KR_{4DMN}$ peptide, no significant change in fluorescence was observed at any pH. The fluorophore remained intact throughout the 24 hr duration. This difference between the stability of 4DMN and that of 4DMAP is most evident at pH 8 where the rate of hydrolysis for 4DMAP is greatest (FIG. 7). The measured fluorescence intensity for the $KR_{4DMN}$ peptide shows little change while greater than 90% of the initial fluorescence of the $KR_{4DMAP}$ peptide was lost.

EXAMPLE 4

Figure 8:
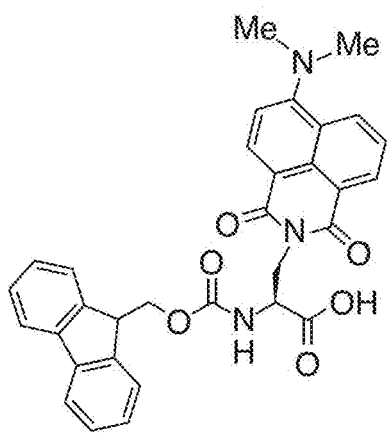
FIG. 8 illustrates Fmoc-4DMNA.

This example illustrates the incorporation of 4DMAP and 6DMN into peptides by coupling an anhydride precursor of either fluorophore to a free amine on a fully synthesized peptide in the last step prior to cleaving the peptide from the solid support. The Fmoc-4DMNA amino acid (FIG. 8) has been used extensively in the preparation of various peptides (data not shown) and has thus far shown no susceptibility to nucleophilic attack by bases like 4-methylpiperidine. This is evident in the experiment shown in FIG. 9 where the KR peptides of 4DMN and 6DMN were both exposed to a standard Fmoc deprotection protocol while still on solid support. Roughly 20 mg of resin for each peptide was transferred to a small 2 mL spin tube and treated at room temperature with a solution of 20% 4-methylpiperidine in DMF (3×5 min). The peptides were then cleaved from the resin and analyzed by MALDI-MS, HPLC, and ESI-MS.

Figure 9A:
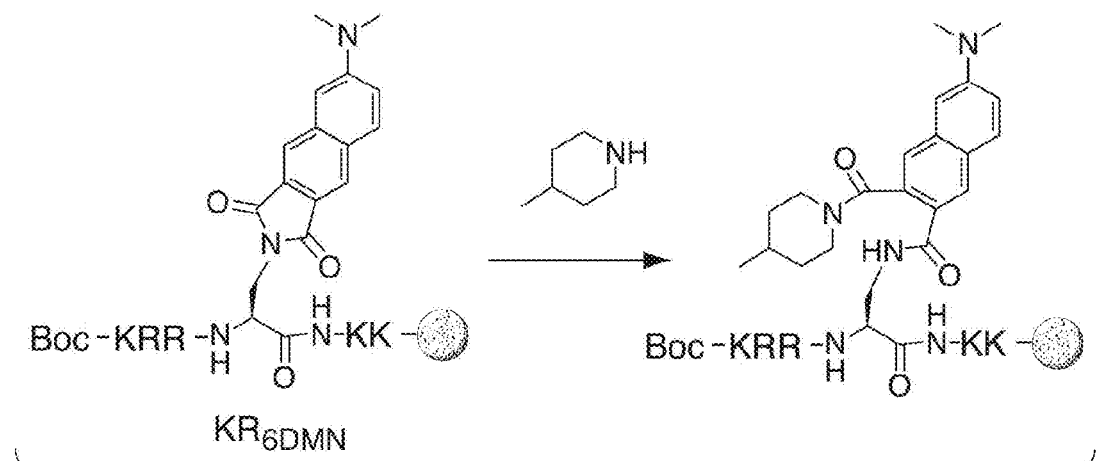
FIGS. 9A-9F illustrate amino acid synthesis using certain compounds.
Figure 9B:
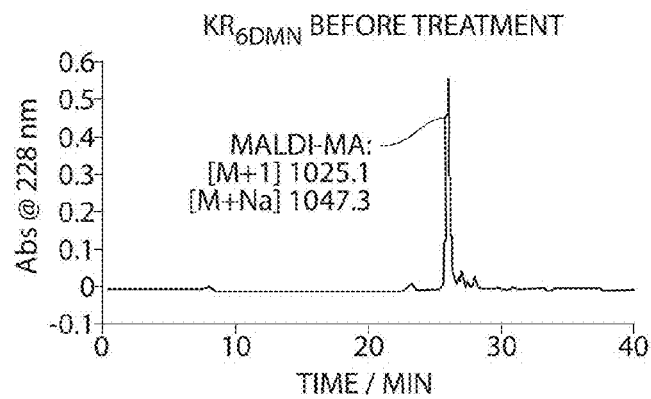
Figure 9C:
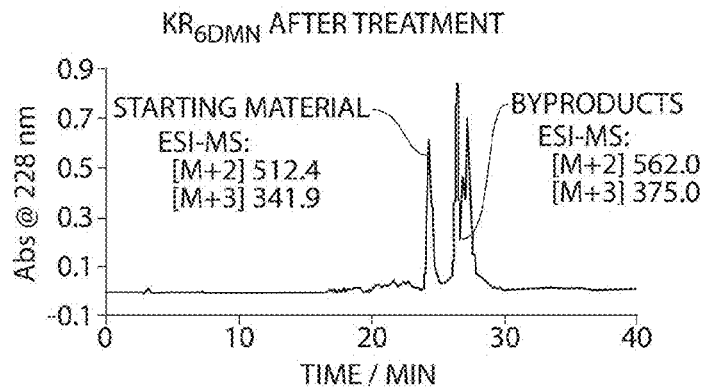
Figure 9D:
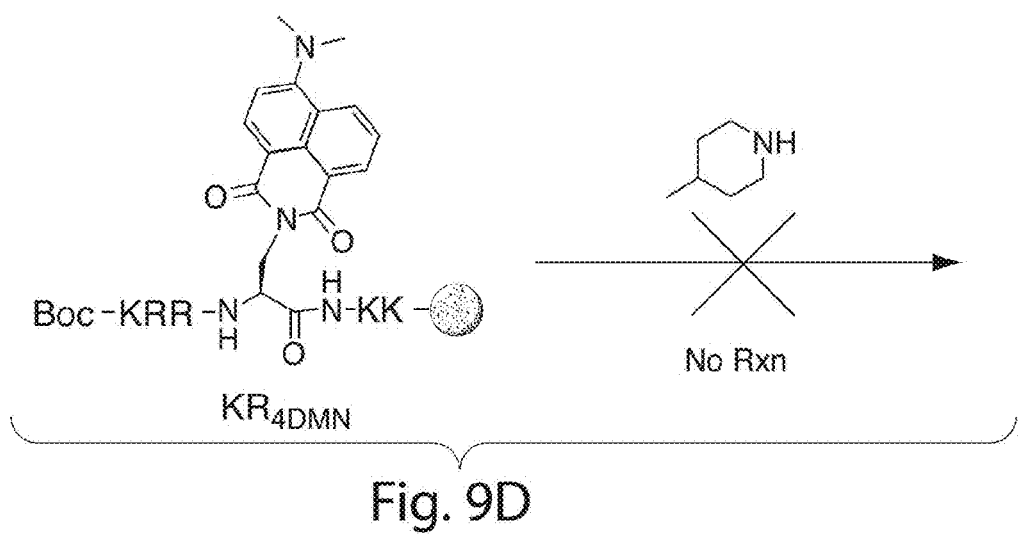
Figure 9E:
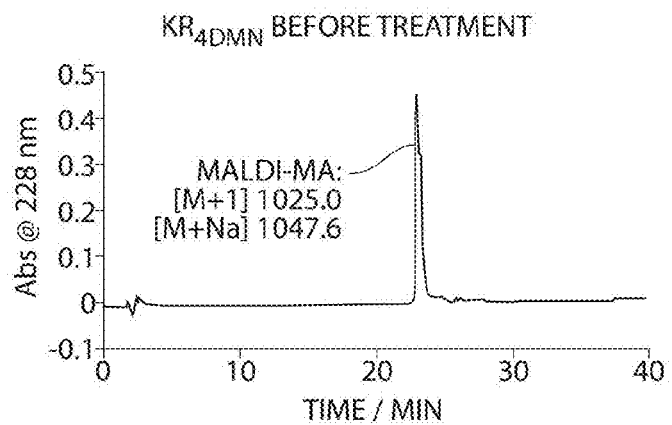
Figure 9F:
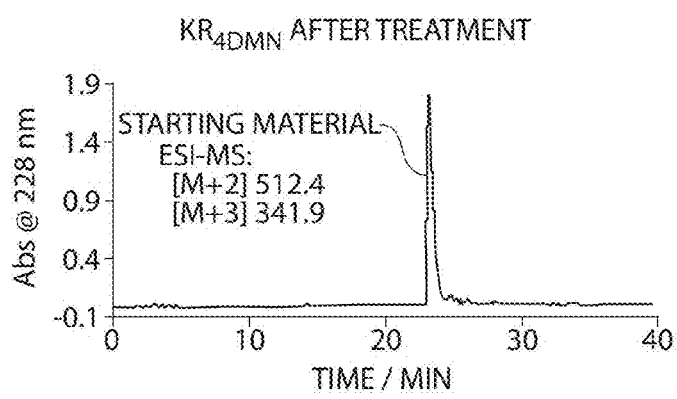

The results of the MALDI-MS data show prominent peaks corresponding to the 4-methylpiperidine adduct for $KR_{6DMN}$. Furthermore, HPLC traces of the base treated $KR_{6DMN}$ peptide exhibited the appearance of two new peaks that elute later than the starting material (FIGS. 9B-9C). The masses of these two peaks determined by ESI-MS were identical and confirmed to be that of the 4-methylpiperidine adduct. It is believed that the occurrence of the two byproduct peaks, instead of one, is due to varying retention times for the two possible isomers formed depending on which of the imide carbonyls are attacked by the base. The same study performed on the $KR_{4DMAP}$ peptide produced identical results (data not shown). By contrast, MALDI-MS data on the treated $KR_{4DMN}$ peptide showed no sign of a 4-methylpiperidine adduct (FIGS. 9D-9F). The HPLC and ESI-MS analysis also confirmed that no reaction occurred. The 4DMNA amino acid appears to be unreactive under these conditions. Furthermore, it is worth emphasizing that the 4DMN chromophore was exposed to this same treatment twice previously during the preparation of the $KR_{4DMN}$ peptide using the 4DMNA Fmoc building-block. Hence, unlike the amino acids of 4DMAP and 6DMN, it appears to be compatible with standard solid phase peptide synthesis.

EXAMPLE 5

Figure 10A:
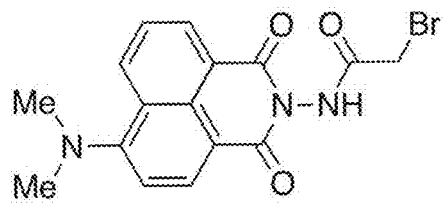
FIGS. 10A-10E illustrate various derivatives in various embodiments of the invention.
Figure 10B:
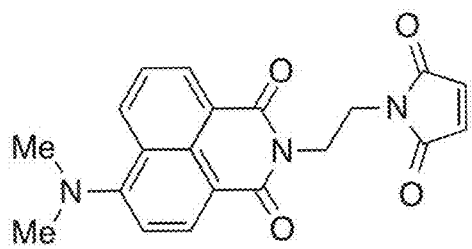
Figure 10C:
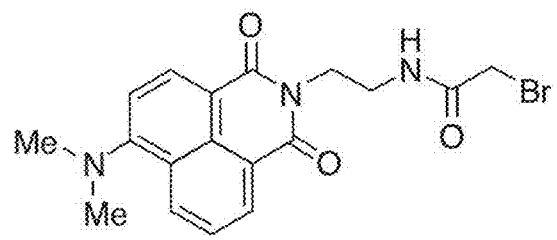
Figure 10D:
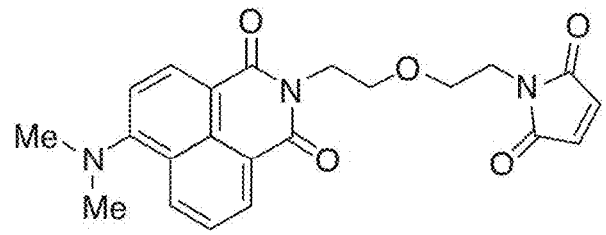
Figure 10E:
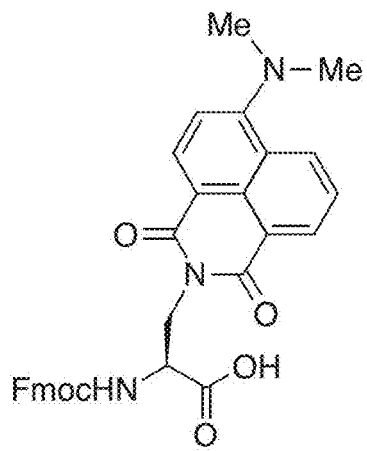

This example illustrates the synthesis of various 4DMN derivatives. FIGS. 10A-10D represent the new series of cysteine modifying agents for use in investigations involving protein/protein interactions and changes in protein allostery. FIG. 10E is the Fmoc amino acid of 4DMN for solid phase peptide synthesis. The synthesis of each agent is depicted schematically in FIGS. 11A-11C.

Figure 11A:
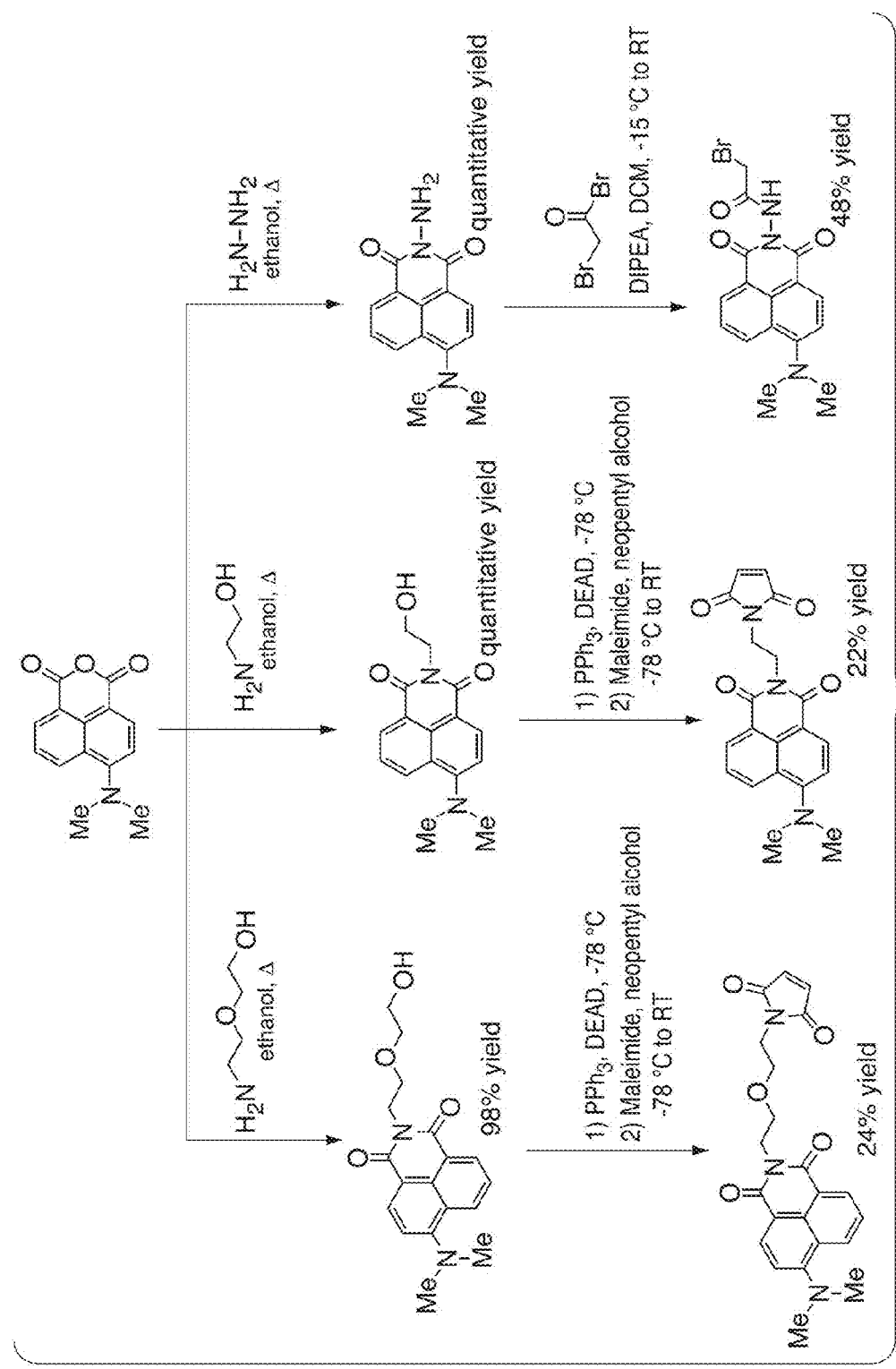
FIGS. 11A-11C illustrate the synthesis of various compounds of the invention.
Figure 11B:
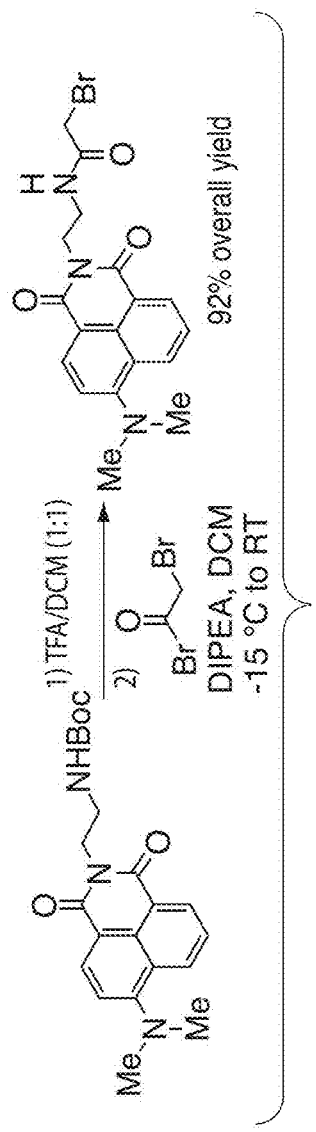
Figure 11C:
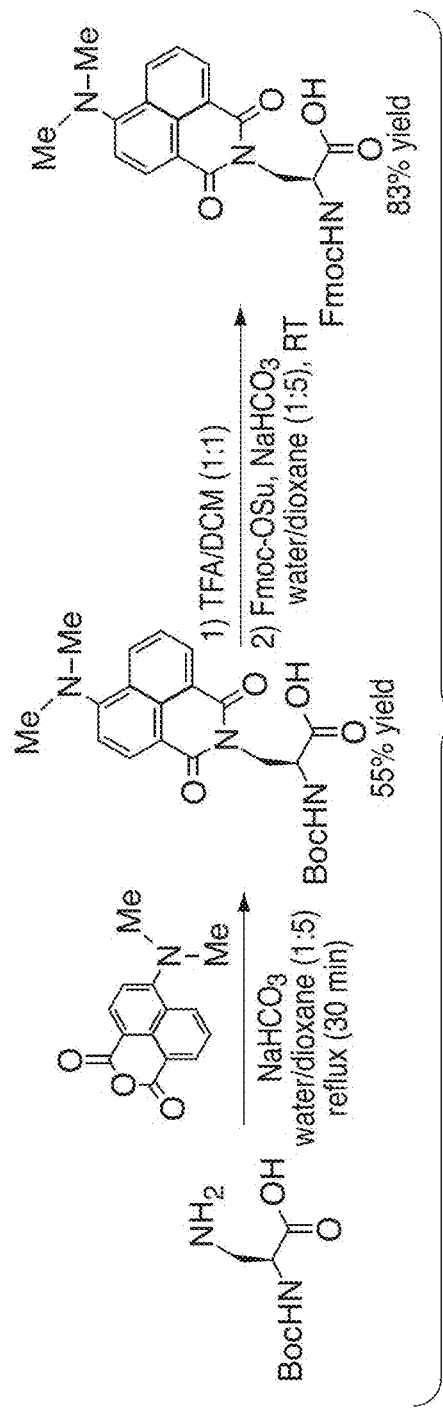

In FIG. 11A, note that the Mitsunobu reaction used to prepare the two maleimide derivatives shown above utilize the method described by Walker (*J. Org. Chem.* 1995, 60, 5352-5355). The 4DMN anhydride shown top was prepared according to the method described by Kollar et. al. (*J. Photochem. Photobiol. A: Chem.* 2005, 170, 151-159).

EXAMPLE 6

This example illustrates the synthesis of various cysteine modifying reagents. These compounds are also shown in FIG. 12.

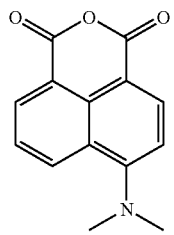 [SMILES: CN(C)c1ccc2c3c(cccc13)C(=O)OC2=O]

4-N,N-dimethylamino-1,8-naphthalic Anhydride

The reagents were initially prepared by previously described methods of Kollar, J., P. Hrdlovic, et al. (2005), "Synthesis and transient absorption spectra of derivatives of 1,8-naphthalic anhydrides and naphthalimides containing 2,2,6,6-tetramethylpiperidine; triplet route of deactivation." *Journal of Photochemistry and Photobiology A: Chemistry* 170(2): 151-159.

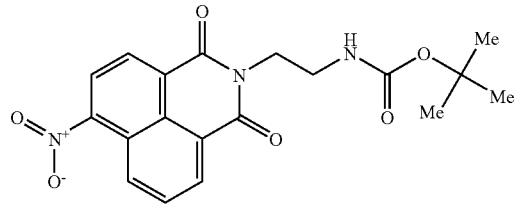 [SMILES: CC(C)(C)OC(=O)NCCN1C(=O)c2cccc3c([N+](=O)[O-])ccc(c23)C1=O]

4-Nitro-N-(2-tert-butoxycarbonylamino-ethyl)-1,8-naphthalimide (1)

Initially, 4-nitro-1,8-naphthalic anhydride (9.2 g, 37.7 mmol) was dissolved in 50 mL of DMF, then DIPEA (17.9 mL, 102.9 mmol) was added. In a separate flask, N-Boc-ethylenediamine was dissolved in another 50 mL DMF and added over 4 mins to the solution containing the anhydride via an addition funnel. The reaction was allowed to proceed for 1 hr at ambient temperature before adding the coupling reagents HOBt/HBTU (100 mL, 0.58 M each in DMF) to facilitate ring closure. The reaction was allowed to proceed overnight. The next day, the reaction mixture was poured into a large separatory funnel containing 400 mL of diethyl ether and washed with brine (3×200 mL) to remove DMF. The organic layer was then dried with $MgSO_4$, filtered, and concentrated to dryness. The crude product was then purified by flash column chromatography using 1:1 hexanes/ethyl acetate to give a light cream colored solid (9.56 g, 24.8 mmol, 72.3% yield). $^1$H-NMR (300 MHz, $CDCl_3$, δ): 1.22 (s, 9H), 3.54 (m, 2H), 4.35 (t, 2H, J=5.7 Hz), 4.96 (m, 1H), 7.96 (dd, 1H, $J_1$=8.7 Hz, $J_2$=7.5 Hz), 8.38 (d, 1H, J=7.8 Hz), 8.66 (d, 1H, J=8.1 Hz), 8.70 (dd, 1H, $J_1$=7.2 Hz, $J_2$=0.9 Hz), 8.79 (dd, 1H, $J_1$=8.7 Hz, $J_2$=0.6 Hz). $^{13}$C-NMR (300 MHz, $CDCl_3$, δ): 28.4, 39.4, 40.8, 79.5, 123.1, 123.8, 124.2, 127.1, 129.4, 129.6, 130.2, 132.8, 149.8, 156.4, 163.1, 163.9.

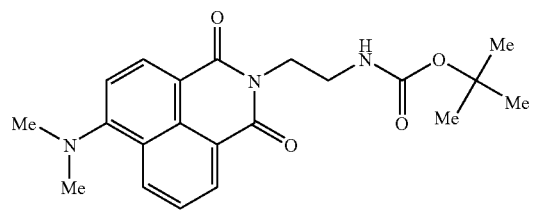 [SMILES: CN(C)c1ccc2c3c(cccc13)C(=O)N(CCNC(=O)OC(C)(C)C)C2=O]

4-N,N-Dimethylamino-N-(2-tert-butoxycarbonylamino-ethyl)-1,8-naphthalimide (2)

The 4-nitro-N-(2-tert-butoxycarbonylamino-ethyl)-1,8-naphthalimide, 1, (2.00 g, 5.19 mmol) was added to a 250 mL two-necked round-bottom flask equipped with a reflux condenser, rubber septum, and magnetic stir bar. The assembled reaction vessel was then charged with and inert atmosphere by evacuating the air under reduced pressure and purging with $N_2$ gas (3×). The flask then received 52 mL of isoamyl alcohol transferred by syringe through the rubber septum. The suspension was stirred as the temperature was raised to 132° C. Once the starting material dissolved, 3-dimethylamino-propionitrile (2.345 mL, 20.76 mmol) was added by syringe through the septum of the reaction vessel. The reaction was refluxed for 22 hrs before stopping by concentrating the reaction mixture to dryness on the rotavap. The crude was then purified by flash chromatography using 3:2 hexanes/ethyl acetate to give an orange solid (1.47 g, 3.83 mmol, 74% yield). $^1$H-NMR (300 MHz, CDCl$_3$, δ): 1.31 (s, 9H), 3.09 (s, 6H), 3.51 (m, 2H), 4.32 (t, 2H, J=5.7 Hz), 5.15 (b, 1H), 7.07 (d, 1H, J=8.1 Hz), 7.61 (dd, 1H, J$_1$=8.4 Hz, J$_2$=7.2 Hz), 8.39 (dd, 1H, J$_1$=8.5 Hz, J$_2$=1.1 Hz), 8.43 (d, 1H, J=8.4 Hz), 8.52 (dd, 1H, J$_1$=7.4 Hz, J$_2$=1.1 Hz). $^{13}$C-NMR (300 MHz, CDCl$_3$, δ).

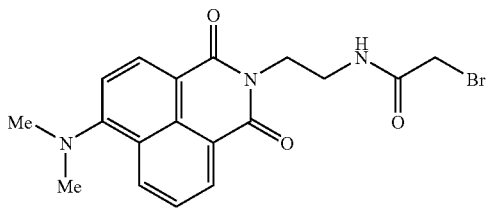 [SMILES: CN(C)c1ccc2c3c(cccc13)C(=O)N(CCNC(=O)CBr)C2=O]

4-N,N-Dimethylamino-N-[2-(2-bromo-acetylamino)-ethyl]-1,8-naphthalimide (3)

2 (0.50 g, 1.30 mmol) was dissolved in dichloromethane (22 mL) in a 100 mL round-bottom flask. Cold trifluoroacetic acid (22 mL) was then added slowly over 5 min by addition funnel while stirring the reaction. The reaction was allowed to proceed at room temperature for 1.5 hrs before concentrating to dryness on the rotavap. The crude solid was redissolved in dichloromethane (100 mL) and washed with 2% NaHCO$_3$ aq. solution (100 mL). The aqueous layer was back-extracted with fresh dichloromethane (2×100 mL) and the organic layers were combined (total volume of 300 mL). The organic layer was dried with MgSO$_4$, filtered and concentrated to give the free amine as an orange solid. The free base was then re-dissolved in dichloromethane (26 mL) in a 100 mL Schlenk flask and cooled to −15° C. in a 1:3 sodium chloride/ice bath. The bromoacetyl bromide (0.17 mL, 1.96 mmol) was then added slowly by syringe followed by DIPEA (0.250 mL, 1.43 mmol). The reaction was allowed to run for 5 min at −15° C. before allowing to rise to room temperature. The reaction was then run for an additional 1.5 hrs. The reaction was stopped by diluting with dichloromethane (100 mL total volume) and washing with 2% NaHCO$_3$ (100 mL), and again with brine (100 mL). The organic layer was then dried with MgSO$_4$, filtered and concentrated to dryness. The crude was then purified by flash column chromatography using ethyl acetate and hexanes to yield a red-orange solid (0.48 mg, 1.19 mmol, 91% yield). $^1$H-NMR (300 MHz, CDCl$_3$, δ): 3.15 (s, 6H), 3.68 (m, 2H), 3.79 (s, 2H), 4.45 (m, 2H), 7.16 (d, 1H, J=8.4 Hz), 7.69 (dd, 1H, J$_1$=8.6 Hz, J$_2$=7.4 Hz), 8.50 (d, 1H, J=8.1 Hz), 8.51 (dd, 1H, J$_1$=8.4 Hz, J$_2$=1.2 Hz), 8.60 (J$_1$=7.2 Hz, J$_2$=1.2 Hz). $^{13}$C-NMR (300 MHz, CDCl$_3$, δ): HRMS-ESI (m/z): [M+H$^+$] calcd for C$_{18}$H$_{18}$BrN$_3$O$_3$ 404.0610, found 404.0613.

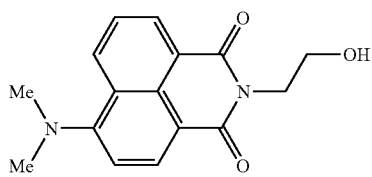 [SMILES: CN(C)c1ccc2c3c(cccc13)C(=O)N(CCO)C2=O]

4-N,N-Dimethylamino-N-(2-hydroxy-ethyl)-1,8-naphthalimide (4)

4-N,N-dimethylamino-1,8-naphthalic anhydride, (1.00 g, 4.15 mmol) was added to a 200 mL two-necked round-bottom flask equipped with a reflux condenser, magnetic stir bar, and rubber septum. The air was then evacuated from the reaction vessel by applying vacuum and replacing with N$_2$ gas (3×). Anhydrous ethanol (42 mL) was then added to the flask by syringe. The suspension was stirred as the temperature was raised to reflux. The anhydride was still present as a suspension at reflux until the addition of ethanolamine (0.28 mL, 4.56 mmol) by syringe. At this point, the slurry becomes a clear deep orange solution. The reaction is allowed to proceed at reflux for 1.5 hrs the stopped by removing the heat source and allowing to cool to room temperature. The solvent is then removed using a rotavap and the crude placed on the high vacuum line overnight to remove excess ethanolamine. The product obtained was an orange solid that required no further purification (1.18 g, 4.15 mmol, quantitative yield). $^1$H-NMR (300 MHz, CDCl$_3$, δ): 3.11 (s, 6H), 3.96 (t, 2H, J=5.3 Hz), 4.43 (t, 2H, J=5.1 Hz), 7.07 (d, 1H, J=8.1 Hz), 7.63 (dd, 1H, J$_1$=8.6 Hz, J$_2$=7.4 Hz), 8.41 (dd, 2H, J$_1$=8.4 Hz, J$_2$=1.2 Hz), 8.43 (d, 1H, J=8.4 Hz), 8.53 (dd, 1H, J$_1$=7.5 Hz, J$_2$=1.2 Hz). $^{13}$C-NMR (300 MHz, CDCl$_3$, δ): 165.8, 165.3, 157.5, 133.3, 131.8, 131.6, 130.6, 125.3, 125.1, 123.0, 114.6, 113.5, 62.4, 45.1, 43.0. HRMS-ESI (m/z): [M+Na$^+$] calcd for C$_{16}$H$_{16}$N$_2$O$_3$ 307.1053, found, 307.1059.

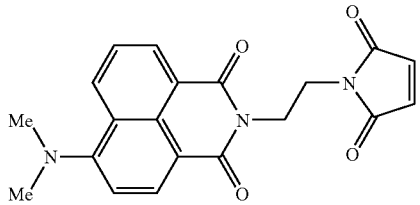 [SMILES: CN(C)c1ccc2c3c(cccc13)C(=O)N(CCN1C(=O)C=CC1=O)C2=O]

4-N,N-Dimethylamino-N-(2-maleimidyl-ethyl)-1,8-naphthalimide (5)

Solid triphenylphosphine (0.42 g, 1.60 mmol) was added to an oven-dried 100 mL Kjeldahl-style Schlenk flask equipped with a magnetic stir bar and rubber septum. The flask was evacuated of air under high vacuum and charged with N$_2$ gas (3×). The triphenylphosphine was then dissolved in freshly distilled anhydrous THF. The solution was then cooled to −78° C. immersing the Schlenk flask in a dry ice/isopropanol bath. Next, diethyl azodicarboxylate (0.696 mL, 40% solution in toluene, 1.60 mmol) was added dropwise via syringe over 1.5 mins. The mixture was allowed to stir for approximately 5 mins to allow formation of the betaine. At this point, the reaction mixture was a pale yellow color. The alcohol, 4 (0.50 g, 1.8 mmol), was then added as a solid followed by neopentyl alcohol (0.07 g, 0.8 mmol) to form the oxyphosphonium ion intermediate. Once the two alcohols were fully dissolved, maleimide was added as a solid and the reacting mixture was allowed to warm to room temperature. The reaction was allowed to proceed at room temperature overnight before concentrating the reaction mixture to dryness using a rotary evaporator. TLC indicated that the reaction only proceeded 30-40%. The product was isolated by flash column chromatography using toluene with 5% methanol. The product was a bright yellow solid (0.13 g, 0.36 mmol, 22.4% yield) and was dissolved in DMSO for storage at −80° C. in 100 mM aliquots. $^1$H-NMR (300 MHz, CDCl$_3$, δ): 3.07 (s, 6H), 3.95 (t, 2H, J=5.1 Hz), 4.37 (t, 2H, J=5.1 Hz), 6.59 (s, 2H), 7.05 (d, 1H, J=8.1 Hz), 7.59 (dd, 1H, J$_1$=8.6 Hz, J$_2$=7.4 Hz), 8.37 (d, 1H, J=8.1 Hz), 8.39 (dd, 1H, J$_1$=8.6 Hz, J$_2$=1.1 Hz), 8.47 (dd, 1H, J$_1$=7.2 Hz, J$_2$=1.2 Hz). $^{13}$C-NMR (300 MHz, CDCl$_3$, δ): 36.5, 38.9, 45.0, 113.5, 114.7, 122.8, 125.1, 125.4, 130.6, 131.3, 131.6, 133.0, 134.3, 157.2, 164.4, 165.0, 171.0.

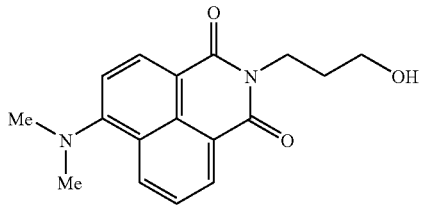 [SMILES: CN(C)c1ccc2c3c(cccc13)C(=O)N(CCCO)C2=O]

4-N,N-Dimethylamino-N-(3-hydroxy-propyl)-1,8-naphthalimide (6)

4-N,N-dimethylamino-1,8-naphthalic anhydride (1.00 g, 4.15 mmol) was added to a 200 mL two-necked round-bottom flask equipped with a reflux condenser, magnetic stir bar, and rubber septum. The air was then evacuated from the reaction vessel by applying vacuum and replacing with N$_2$ gas (3×). Anhydrous ethanol (42 mL) was then added to the flask by syringe. The suspension was stirred as the temperature was raised to reflux. The anhydride was still present as a suspension at reflux until the addition of 3-amino-1-propanol (0.347 mL, 4.56 mmol) by syringe. At this point, the slurry becomes a clear deep orange solution. The reaction was allowed to proceed at reflux for 1.5 hrs the stopped by removing the heat source and allowing to cool to room temperature. The solvent was then removed using a rotavap and the crude placed on the high vacuum line overnight to remove excess 3-amino-1-propanol. The product obtained was an orange solid that required no further purification (1.17 g, 4.13 mmol, 99.5% yield). $^1$H-NMR (300 MHz, CDCl$_3$, δ): 1.98 (m, 2H), 3.14 (s, 6H), 3.56 (t, 2H, J=5.6 Hz), 3.45 (t, 2H, J=6.0 Hz), 7.13 (d, 1H, J=8.4 Hz), 7.68 (dd, 1H, J$_1$=8.4 Hz, J$_2$=7.2 Hz), 8.47 (dd, 1H, J$_1$=8.4 Hz, J$_2$=1.2 Hz), 8.49 (d, 1H, J=8.4 Hz), 8.59 (dd, 1H, J$_1$=7.2 Hz, J$_2$=1.2 Hz). $^{13}$C-NMR (300 MHz, CDCl$_3$, δ):

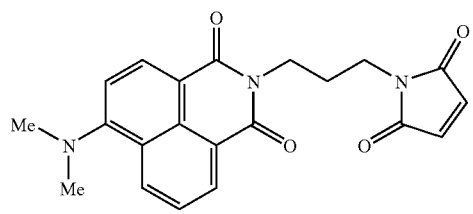 [SMILES: CN(C)c1ccc2c3c(cccc13)C(=O)N(CCCN1C(=O)C=CC1=O)C2=O]

4-N,N-Dimethylamino-N-(3-maleimidyl-propyl)-1,8-naphthalimide (7)

Solid triphenylphosphine (0.40 g, 1.52 mmol) was added to an oven-dried 100 mL Kjeldahl-style schlenk flask equipped with a magnetic stir bar and rubber septum. The flask was evacuated of air under high vacuum and charged with N$_2$ gas (3×). The triphenylphosphine was then dissolved in freshly distilled anhydrous THF (4 mL). The solution was then cooled to −78° C. immersing the schlenk flask in a dry ice/isopropanol bath. Next, diethyl azodicarboxylate (0.664 mL, 40% solution in toluene, 1.52 mmol) was added dropwise via syringe over 1.5 mins. The mixture was allowed to stir for approximately 5 mins to allow formation of the betaine. At this point, the reaction mixture was a pale yellow color. The alcohol, 6 (0.50 g, 1.68 mmol), was then added as a solid followed by neopentyl alcohol (0.07 g, 0.76 mmol) to form the oxyphosphonium ion intermediate. Once the two alcohols were fully dissolved, maleimide (0.15 g, 1.52 mmol) was added as a solid and the reacting mixture was allowed to warm to room temperature. The reaction was allowed to proceed at room temperature overnight before concentrating the reaction mixture to dryness using a rotary evaporator. The product was isolated by flash column chromatography using hexanes and ethyl acetate. The product was a bright yellow solid (0.02 g, 0.05 mmol, 3.2% yield).

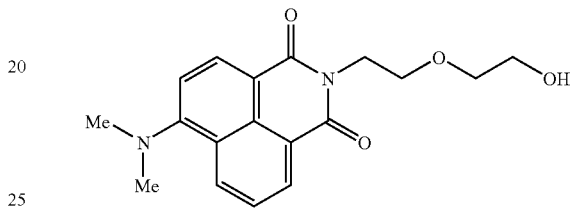

4-N,N-Dimethylamino-N-[2-(2-hydroxy-ethoxy)-ethyl]-1,8-naphthalimide (8)

4-N,N-dimethylamino-1,8-naphthalic anhydride (1.00 g, 4.15 mmol) was added to a 200 mL two-necked round-bottom flask equipped with a reflux condenser, magnetic stir bar, and rubber septum. The air was then evacuated from the reaction vessel by applying vacuum and replacing with N$_2$ gas (3×). Anhydrous ethanol (42 mL) was then added to the flask by syringe. The suspension was stirred as the temperature was raised to reflux. The anhydride was still present as a suspension at reflux until the addition of 2-(2-aminoethoxy)-ethanol (0.454 mL, 4.56 mmol) by syringe. At this point, the slurry becomes a clear deep orange solution. The reaction was allowed to proceed at reflux for 1.5 hrs, then stopped by removing the heat source and allowing to cool to room temperature. The solvent was then removed using a rotavap and the crude placed on the high vacuum line overnight to remove excess 2-(2-aminoethoxy)-ethanol. The product obtained was orange-brown oil that required no further purification (1.33 g, 4.05 mmol, 97.7% yield). $^1$H-NMR (300 MHz, CDCl$_3$, δ): $^{13}$C-NMR (300 MHz, CDCl$_3$, δ): 39.3, 44.7, 61.8, 68.5, 72.4, 113.1, 114.3, 122.6, 124.7, 124.9, 130.1, 131.1, 131.3, 132.8, 156.9, 164.1, 164.7

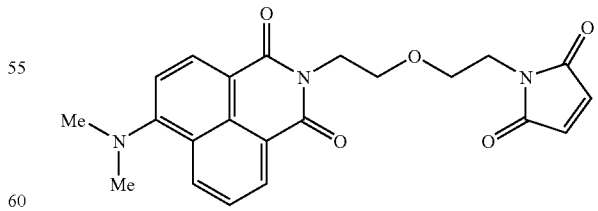

4-N,N-Dimethylamino-N-[2-(2-maleimidyl-ethoxy)-ethyl]-1,8-naphthalimide (9)

Prior to setting up the Mitsunobu reaction, the 4-N,N-dimethylamino-N-[2-(2-hydroxy-ethoxy)-ethyl]-1,8-naphthalimide (0.50 g, 1.51 mmol) was transferred to a 50 mL pear-shaped flask equipped with rubber stopper and placed under high vacuum overnight to remove residual water. An oven-dried 100 mL Kjeldahl-style Schlenk flask equipped with a magnetic stir bar and rubber septum was charged with solid triphenylphosphine (0.36 g, 1.37 mmol). The Schlenk flask was then evacuated of air by placing under high vacuum and purging with $N_2$ gas (3× freshly distilled dry THF (4 mL) was then transferred to the Schlenk flask by syringe and the triphenylphosphine stirred at ambient temperature until completely dissolved. This solution was then lowered to −78° C. by immersing in a dry ice/isopropanol bath. Next, diethyl azodicarboxylate (0.597 mL, 40% solution in toluene, 1.37 mmol) was added dropwise via syringe over 2 mins. The mixture was allowed to stir for approximately 5 mins to allow formation of the betaine. At this point, the reaction mixture was a pale yellow color. Meanwhile, a solution of the alcohol, 8, was prepared by dissolving in 6 mL of freshly distilled dry THF. This solution was then transferred very slowly to the reaction vessel by syringe to avoid raising the temperature. Once this transfer was complete, neopentyl alcohol (0.06 g, 0.69 mmol) was added as a solid. The reaction was allowed to stir approximately 5 min to allow formation of the oxyphosphonium ion intermediate. Solid maleimide (0.13 g, 1.37 mmol) was then added and the reaction was allowed to warm to room temperature and stir overnight. The reaction was stopped by concentrating to dryness on the rotary evaporator and the product was isolated by flash column chromatography using 1:2 hexanes/ethyl acetate. The product was a bright yellow solid (0.15 g, 0.37 mmol, 24.4% yield) and was dissolved in DMSO for storage at −80° C. in 100 mM aliquots. $^1$H-NMR (300 MHz, $CDCl_3$, δ): 3.10 (s, 6H), 3.66 (m, 4H), 3.75 (t, 2H, J=6.0 Hz), 4.35 (t, 2H, J=6.0 Hz), 6.51 (s, 2H), 7.10 (d, 1H, J=8.1 Hz), 7.64 (dd, 1H, $J_1$=8.4 Hz, $J_2$=7.2 Hz), 8.43 (m, 2H), 8.52 (dd, 1H, $J_1$=7.5 Hz, $J_2$=1.2 Hz). $^{13}$C-NMR (300 MHz, $CDCl_3$, δ): 37.5, 39.1, 45.1, 67.6, 67.9, 113.6, 115.2, 123.2, 125.2, 125.5, 130.5, 131.4, 131.4, 133.0, 134.2, 157.0, 164.2, 164.8, 170.9.

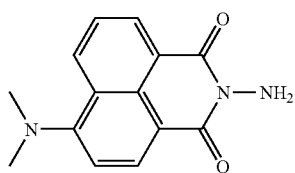 [SMILES: CN(C)c1ccc2c3c(cccc13)C(=O)N(N)C2=O]

N-amino-4-N,N-dimethylamino-1,8-naphthalimide

Synthesis of this reagent was, in one embodiment, as previously described in Li, C., X. Pan, et al. (2003). "Synthesis of novel copoly(styrene-maleic anhydride) materials and their luminescent properties." *European Polymer Journal* 39(6): 1091-1097. The solid 4-N,N-dimethylamino naphthalic anhydride (0.50 g, 2.07 mmol) was added to a two-necked 100 mL round-bottom flask equipped with a reflux condenser and charged the reaction vessel with $N_2$ gas (3×). Next, ethanol (21 mL) was added and the stirring suspension was heated to reflux. Hydrazine monohydrate (2.08 g, 41.45 mmol) was added by syringe through the rubber septum and the suspension immediately turned clear. The reaction was allowed to proceed for 45 minutes. The temperature was then reduced to 25° C. and the product precipitated by diluting in water and letting stand. The orange solid was collected by filtering (0.31 g, 1.21 mmol, 58% yield). $^1$H-NMR (500 MHz, $CDCl_3$, δ): 2.92 (bs), 3.14 (s, 6H), 7.13 (d, 1H, J=8.4 Hz), 7.68 (dd, 1H, $J_1$=8.6 Hz, $J_2$=7.4 Hz), 8.48 (dd, 1H, $J_1$=8.7 Hz, $J_2$=0.9 Hz), 8.51 (d, 1H, J=8.1 Hz), 8.61 (dd, 1H, $J_1$=7.5 Hz, $J_2$=1.2 Hz).

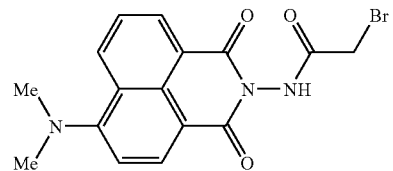 [SMILES: CN(C)c1ccc2c3c(cccc13)C(=O)N(NC(=O)CBr)C2=O]

4-N,N-Dimethylamino-N-[2-bromoacetamido]-1,8-naphthalimide (10)

Solid N-amino-4-dimethylamino-1,8-naphthalimide (0.50 g, 1.96 mmol) was added to a 100 mL Schlenk flask equipped with a magnetic stir bar. The flask was then capped with a rubber septum to be evacuated and flushed with nitrogen gas (3×). Freshly distilled dichloromethane was then transferred to the flask by syringe. The suspension was stirred as DIPEA (375 microliters, 2.16 mmol) was added. The Schlenk flask was then lowered into an ice bath (−15° C.) containing NaCl (about 3:1 by weigh) where the suspension was stirred as the bromoacetyl bromide (255 microliters, 2.94 mmol) was added dropwise over 1 min. The reaction was allowed to proceed at −15° C. before raising it to room temperature and running overnight. The reaction was stopped by washing with 2% $NaHCO_3$ (aq) (3×40 mL). The crude was concentrated on a rotary evaporator and the products isolated by flash column chromatography using 2:1 hexanes/ethyl acetate. The product was a bright orange solid (0.24 g, 0.93 mmol, 48% yield). Note: The yield was due to conversion of the desired product into the diacylated byproduct in the presence of excess bromoacetyl bromide. $^1$H-NMR (300 MHz, $CDCl_3$, δ): 3.14 (s, 6H), 4.14 (s, 2H), 7.09 (d, 1H, J=8.4 Hz), 7.65 (dd, 1H, $J_1$=8.4 Hz, $J_2$=7.5 Hz), 8.45 (dd, 1H, $J_1$=8.4 Hz, $J_2$=1.2 Hz), 8.47 (d, 1H, J=8.1 Hz), 8.58 (dd, 1H, $J_1$=7.4 Hz, $J_2$=1.1 Hz), 8.63 (s, 1H).

Synthesis of the 4DMNA amino acid reagents was as follows.

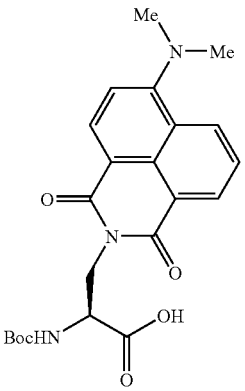 [SMILES: CN(C)c1ccc2c3c(cccc13)C(=O)N(C[C@H](NC(=O)OC(C)(C)C)C(=O)O)C2=O]

N-α-Boc-(4-N,N-dimethylamino-1,8-naphthalimido) alanine (11)

3-amino-2-(Boc-amino)-propionic acid (2.00 g, 9.79 mmol) and $NaHCO_3$ (4.11 g, 48.97 mmol) were dissolved together in dH$_2$O (49 mL) and transferred to a 60 mL addition funnel. Next, added solid 4-N,N-dimethylamino naphthalic anhydride (2.60 g, 10.77 mmol) to a 500 mL three-necked round-bottom flask equipped with a magnetic stir bar and reflux condenser. The reaction vessel was evacuated of air by placing under high vacuum, then charging with N$_2$ gas (3×). Dioxane (245 mL) was then transferred to the reaction vessel via syringe through the rubber septum. The suspension was stirred vigorously as the temperature was raised to reflux. Once at reflux, the aqueous solution of the amino-acid was added slowly over 5 min. The reaction was allowed to proceed at reflux for 30 min before allowing cooling to room temperature. The reaction was then concentrated on the rotary evaporator to remove most of the dioxane before diluting to 200 mL with dH$_2$O and washing with ether to remove unreacted anhydride. The aqueous layer was then acidified with 6 N HCl and extracted with DCM (3×100 mL). The organic layers were combined, dried with MgSO$_4$, filtered, and concentrated. The crude was purified by flash column chromatography using ethyl acetate with 0.5% acetic acid as the solvent system. The fractions containing the desired product were combined and azeotroped in toluene (3×100 mL) to remove residual acetic acid. The product was isolated as a bright orange solid (2.31 mg, 5.40 mmol, 55% yield, R$_f$=0.2 in EtOAc with 0.5% AcOH). $^1$H-NMR (500 MHz, CDCl$_3$, δ): 1.26 (s, 9H), 3.12 (s, 6H), 4.61 (m, 2H), 4.81 (m, 1H), 5.67 (d, 1H, J=7.0 Hz), 7.11 (d, 1H, J=8.5 Hz), 7.65 (apparent triplet, 1H, J=8.0 Hz), 8.44 (d, 1H, J=8.0 Hz), 8.48 (d, 1H, J=8.0 Hz), 8.56 (d, 1H, J=7.0 Hz). $^{13}$C-NMR (300 MHz, CDCl$_3$, δ): 174.0 165.4, 164.9, 157.5, 156.4, 133.6, 132.0, 131.9, 130.8, 125.3, 125.2, 122.8, 114.5, 113.6, 80.6, 53.2, 45.1, 41.0, 28.4. HRMS-ESI (m/z): [M+H$^+$] calcd for C$_{22}$H$_{25}$N$_3$O$_6$ 428.1816, found, 428.1814.

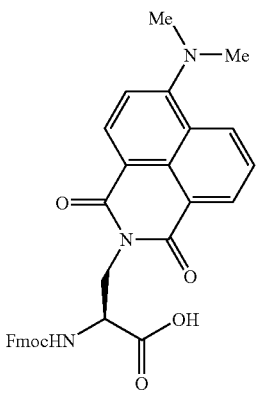

N-α-Fmoc-(4-N,N-dimethylamino-1,8-naphthalimido) alanine (12)

The solid Boc-4DMNA, 11, (2.0 g, 4.68 mmol) was dissolved in dichloromethane (47 mL) and stirred in a 250 mL round-bottom flask as cold TFA (47 mL) was added by addition funnel over 5 min. The reaction was allowed to proceed at ambient temperature for 1.5 hrs before concentrating to dryness and azeotroping with chloroform (3×50 mL) to remove residual TFA. The crude was then placed under high vacuum overnight. The following day, the crude was redissolved in dH$_2$O (23 mL) with NaHCO$_3$ (1.97 g, 23.40 mmol). The pH was tested to ensure the solution was basic. A solution of N-(9-fluorenylmethoxycarbonyloxy) succinimide (1.74 g, 5.15 mmol) was then prepared in dioxane (117 mL) and slowly added to the stirring solution of the amino-acid. The reaction was allowed to proceed for 2 hrs before concentrating to remove most of the dioxane and re-diluting to a total volume of 150 mL in dH$_2$O. The aqueous layer was then washed diethyl ether (1×50 mL) to remove excess Fmoc-OSu. The aqueous layer was then acidified with 6 N HCl and the product extracted into dichloromethane (3×100 mL). The organic layers were then combined, dried with MgSO$_4$, filtered, and concentrated. The product was purified by flash column chromatography using 3:1 ethyl acetate/hexanes with 0.5% acetic acid as the solvent system. The product is an orange solid (2.14 g, 3.89 mmol, 83% yield, R$_f$=0.2 in EtOAc with 5% AcOH). Note: the final product contained approximate 1.6% toluene by mass as a result of azeotroping in toluene to remove residual acetic acid following the purification. $^1$H-NMR (500 MHz, CDCl$_3$, δ): 3.02 (s, 6H), 3.95 (t, 1H, J=7.3 Hz), 4.11 (dd, 1H, J$_1$=10.5 Hz, J$_2$=8.0 Hz), 4.21 (dd, 1H, J$_1$=10.8 Hz, J$_2$=7.3 Hz), 4.72 (d, 2H, J=6.5 Hz), 4.99 (apparent dd, 1H, J$_1$=14.8 Hz, J$_2$=7.3 Hz), 6.17 (d, 1H, J=8.0 Hz), 6.96 (d, 1H, J=8.5 Hz), 7.16 (apparent t, 1H, J=7.5 Hz), 7.21 (apparent t, 1H, J=8.0 Hz), 7.31 (apparent t, 2H, J=7.3 Hz), 7.45 (d, 1H, J=7.5 Hz), 7.5 (d, 1H, J=7.5 Hz), 7.57 (apparent t, 1H, J=8.0 Hz), 7.66 (apparent t, 2H, J=6.5 Hz), 8.34 (d, 1H, J=8.0 Hz), 8.41 (d, 1H, J=8.5 Hz), 8.54 (d, 1H, J=7.5 Hz). $^{13}$C-NMR (500 MHz, CDCl$_3$, δ): 173.9, 165.4, 164.9, 157.5, 156.7, 144.3, 144.0, 141.4, 141.3, 133.8, 132.0, 132.0, 130.7, 127.8, 127.3, 127.3, 125.7, 125.5, 125.1, 125.1, 122.6, 120.0, 120.0, 114.0, 113.4, 67.6, 53.6, 47.2, 44.9, 41.0. HRMS-ESI (m/z): [M+H$^+$] calcd for C$_{32}$H$_{27}$N$_3$O$_6$ 550.1973, found, 550.1959.

Both the $^{13}$C-NMR and $^1$H-NMR of this compound exhibited anisochronous resonances for nine of the ten aromatic carbons and all eight of the aromatic protons of the 9-fluorenyl group. A variable temperature experiment showed no coalescence of these aromatic protons at 80° C. The cause of this apparent asymmetry is believed to be the result of a highly stable conformer in which there exists a partial overlap of one side to the 9-fluorenyl ring system with that of the fluorescent side chain of the amino acid. These nuclei would therefore lack chemical equivalence, thus producing the observed spectra.

EXAMPLE 7

Figure 13A:
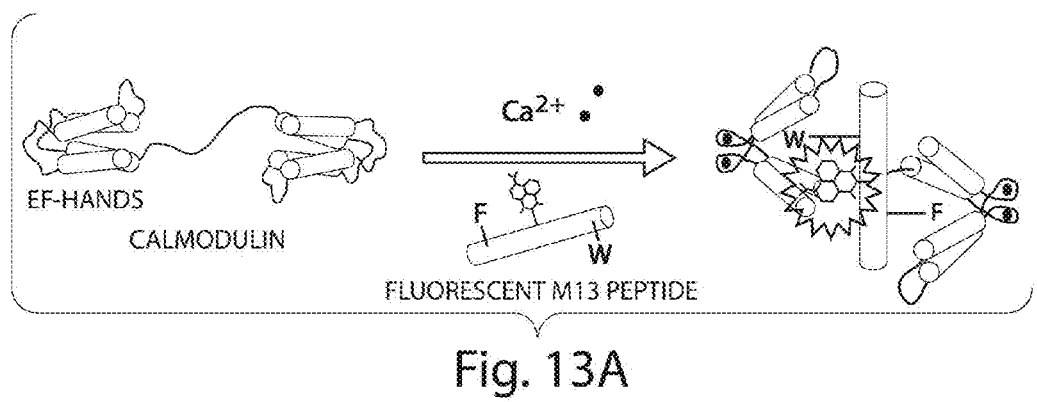
FIGS. 13A-13C illustrate a peptide probe according to one embodiment of the invention.

This example illustrates a peptide probe for detecting calmodulin activation. Calmodulin is a an important calcium sensor found in many cell types that consists of two globular domains located at the N- and C-termini and connected by a flexible linker region. Upon binding Ca$^{2+}$ through specialized loop motifs called EF-hands, the two globular domains undergo an allosteric change that creates two new hydrophobic pockets. These pockets modify the ability of calmodulin to bind its binding partners. Shown in FIG. 13A is a diagram depiction of calmodulin binding to the M13 peptide derived from calmodulin-binding-domain of myosin light-chain kinase. The key recognition elements of this binding interaction are the tryptophan (W) and phenylalanine (F) residues of the M13 peptide spaced 12 residues apart from each other. These are the residues that eventually occupy the two hydrophobic pockets of calmodulin upon Ca$^{2+}$ activation.

Figure 13B:
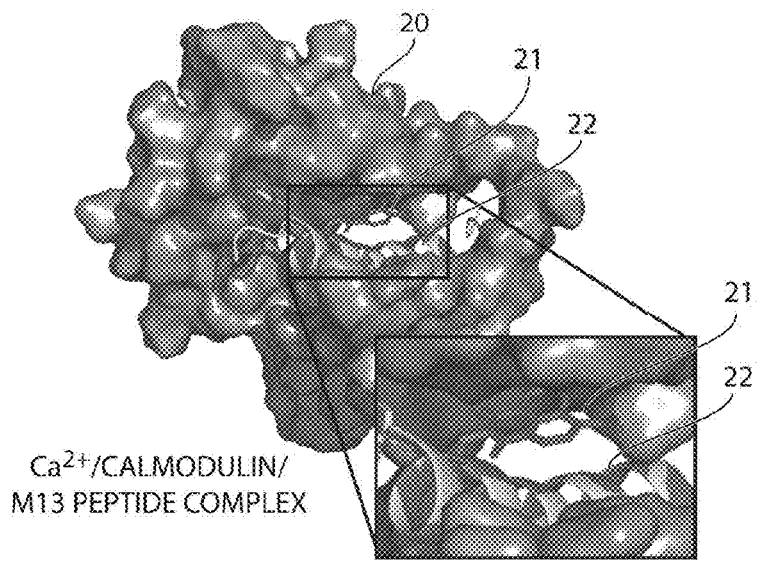
Figure 13C:
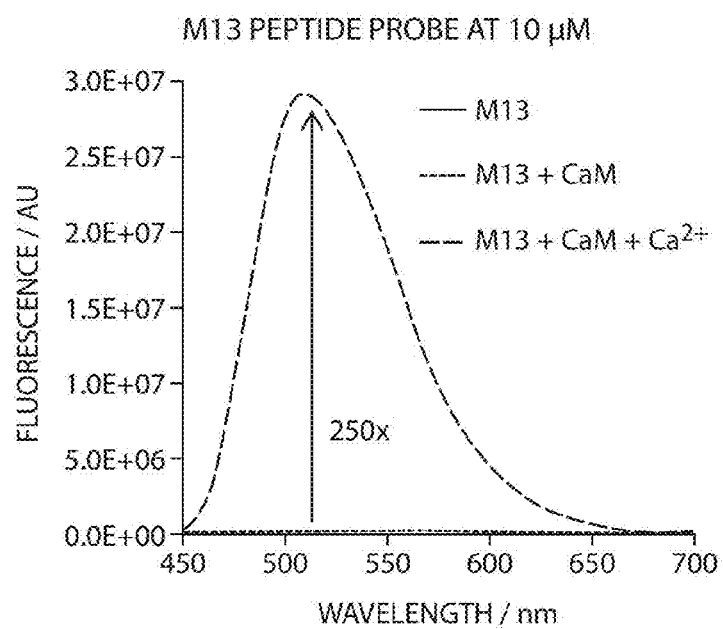
Figure 14A:
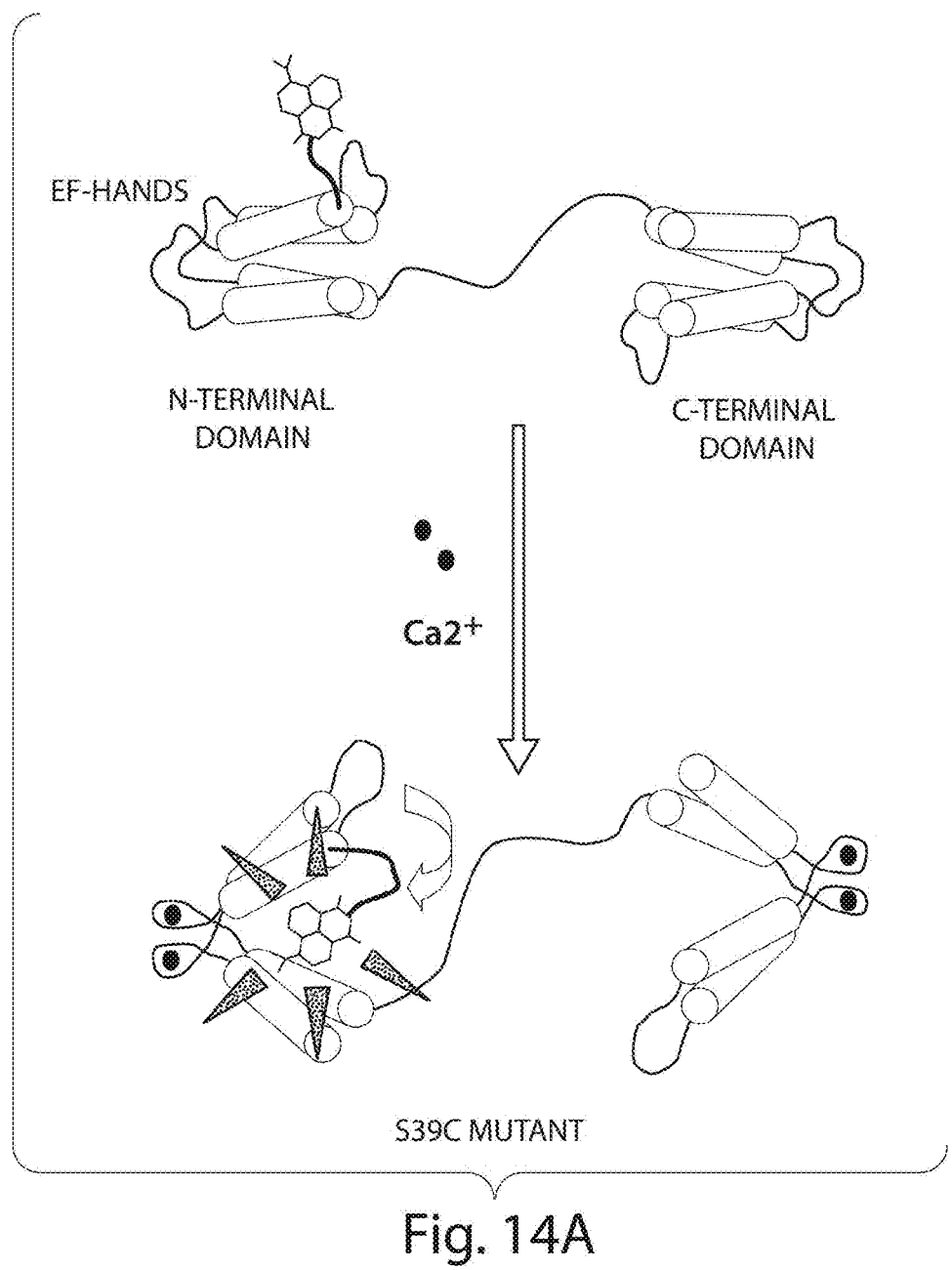
FIGS. 14A-14D illustrate the probing of calmodulin allostery, in another embodiment of the invention.
Figure 14B:
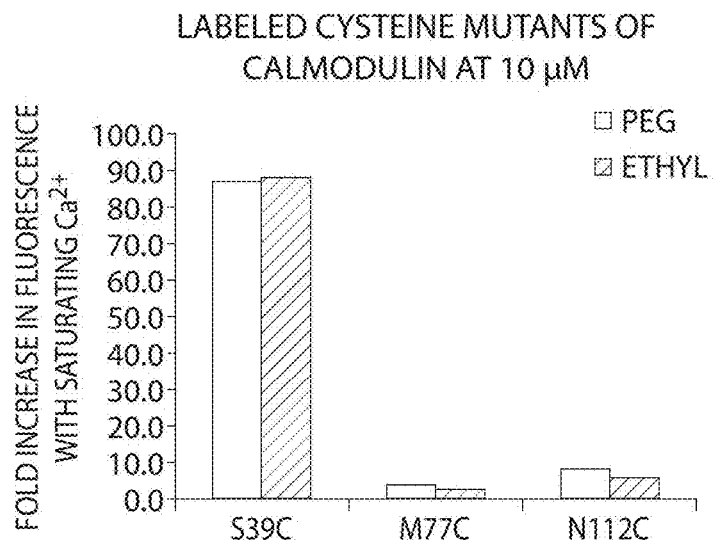
Figure 14C:
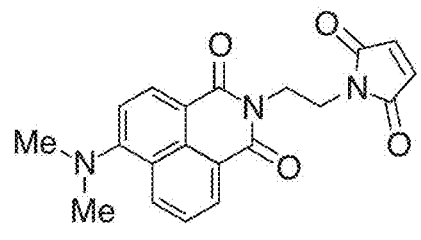
Figure 14D:
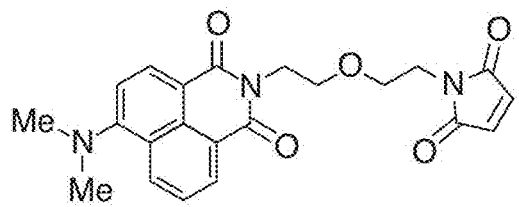

To test the ability of the 4DMNA amino acid to detect such a binding event, it was inserted into the M13 peptide by standard solid phase peptide synthesis such that it was located in the region separating the W and F residues required for binding. The protein structure in FIG. 13B depicts Ca$^{2+}$/calmodulin (20) binding the synthetic M13 peptide (22) with the 4DMNA side chain (21) shown buried where it was predicted in the complex. The graph in FIG. 13C depicts the actual experiment where the fluorescence of the M13 peptide mutant (10 micromolar in TBS pH 7.4) was measured alone, in the presence of saturating calmodulin (15 micromolar), and the presence of both calmodulin (15 micromolar) and a saturating level of calcium chloride (200 micromolar). The figure shows that the 250 fold increase in fluorescence was only obtained in the presence both calmodulin and calcium. A further control (data not shown) showed that the M13 peptide mutant was not responsive to the presence of calcium alone.

EXAMPLE 8

This example illustrates the probing dynamics of calmodulin allostery in presence of $Ca^{2+}$. Calmodulin is a relatively small protein (148 residues) that contains no native cysteines. Therefore, it was possible to prepare a number of cysteine mutants of calmodulin through sight-directed mutagenesis such that the protein could be chemoselectively labeled at virtually any desired position.

This example identifies 4DMN labeled calmodulin mutants that could produce a significant change in fluorescence upon calcium activation. One mutant (S39C) examined in this screen produce a greater than 80 fold increase in fluoresce upon addition of saturating calcium (200 micromolar). The signal response was relatively insensitive to the linker length used (FIG. 14) for the 4DMN maleimide. It is believed that the reason for this fluorescence change is that the fluorophore, tethered to residue 39, is in position to swing into one of the hydrophobic pockets of calmodulin created upon calcium binding. The fluorescently labeled M77C and N112C mutants position the fluorophore such that it can not satisfactorily reach either of the hydrophobic pockets to the same extent as the S39C mutant.

EXAMPLE 9

This example illustrates detection of protein/protein interactions. Work was as performed to identify a cysteine mutant of calmodulin that would selectively detect the interaction of calmodulin with its binding partner. In this case, the binding partner was the wild type M13 peptide ($H_2N$-RRWKKNFIA-VSAANRFKK-$CONH_2$) (SEQ ID NO: 10), which did not contain the 4DMNA amino acid.

Figure 15A:
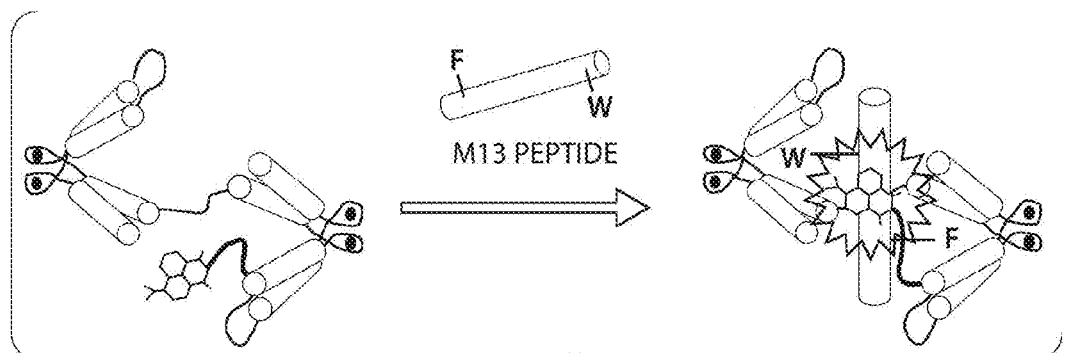
FIGS. 15A-15C illustrate the detection of protein-protein interactions, in yet another embodiment of the invention.
Figure 15B:
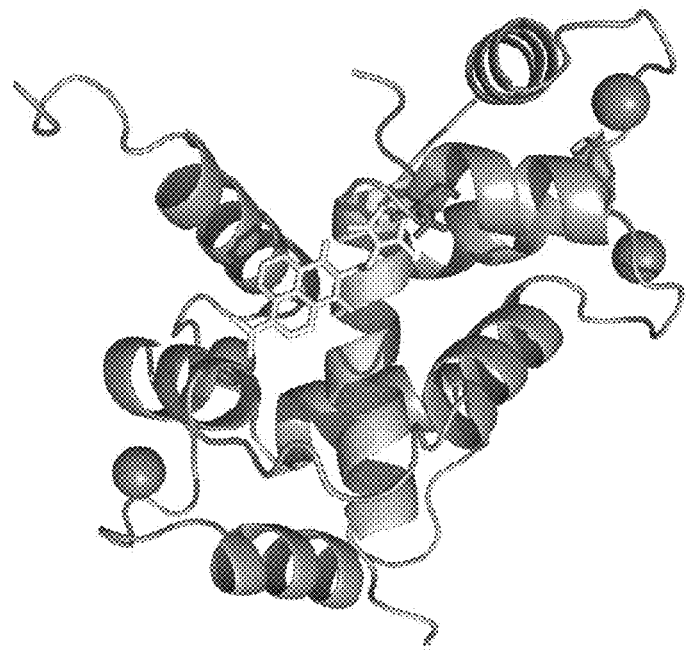
Figure 15C:
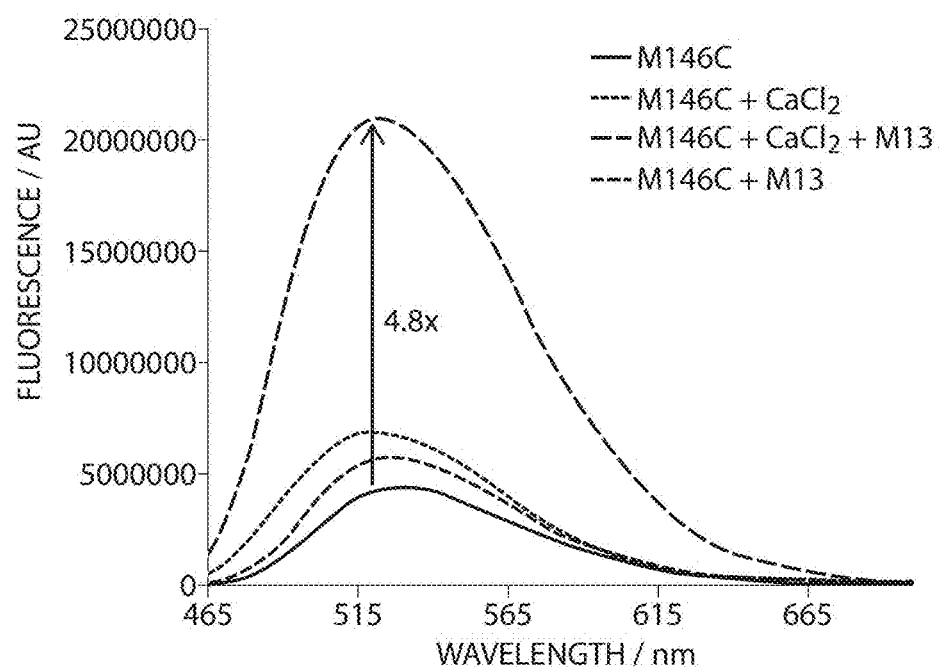

During the screening process, the M146C mutant was identified as possessing the desired fluorescence response profile. The mutant was labeled with the 4DMN maleimide containing the ethyl linker (FIG. 14). The fluorescence of the labeled M146C construct was then measured under four conditions: by itself at 5 micromolar in TBS pH 7.4, in the presence of saturating calcium (200 micromolar), in the presence of the wild type M13 peptide (50 micromolar), and in the presence of both saturating calcium and the wild type M13 peptide. The max fluorescence change was observed only in the presence of bo calcium and the M13 peptide indicating that the fluorophore was likely responding to the bound complex (FIG. 15B).

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An article, comprising:
a compound of formula (I):

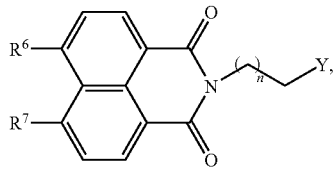

wherein $R^6$ and $R^7$ are independently hydrogen, halogen, alkyl, or —$NR^1R^2$ such that at least one of $R^6$ and $R^7$ is —$NR^1R^2$, $R^1$ and $R^2$ each independently being a substituted or unsubstituted alkyl;
Y is a, —SH, —$NHR^3$, —$C(O)X^1$, -maleimidyl, —$NHCOR^3$, —$NHCO(CH_2)X^2$, or —$CH(NHR^3)COOH$;
$R^3$ is hydrogen, substituted or unsubstituted alkyl, or an N-protecting group;
$X^1$ is hydrogen, halogen, hydroxy, alkoxy, or O-succidimidyl;
$X^2$ is hydrogen, halogen, hydroxy, alkoxy; and
n is 0, 1, 2, or 3.

2. The article of claim 1, wherein the compound has a formula (II):

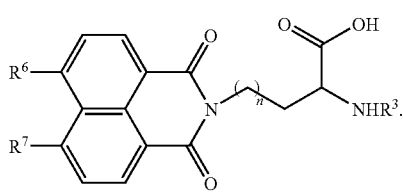

3. The article of claim 1, wherein $R^6$ is —$NR^1R^2$ and $R^7$ is —H.

4. The article of claim 2, wherein the compound has a formula (V):

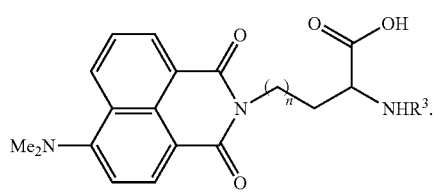

5. The article of claim 2, wherein the compound has a formula (VI):

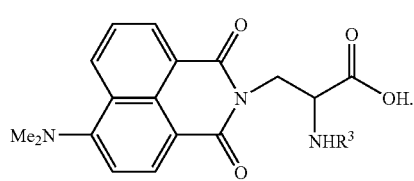

6. The article of claim 5, wherein $R^3$ is H.

7. The article of claim 1, wherein the compound has a formula (VII):

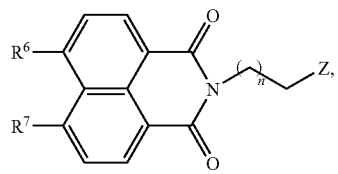

wherein Z is —SH, —$NHR^3$, —$C(O)X^1$, -maleimidyl, —$NHCOR^3$, or —$NHCO(CH_2)X^2$.

8. The article of claim 7, wherein Z is —SH or —$NH_2$.

9. The article of claim 7, wherein the compound has a formula (VIII):

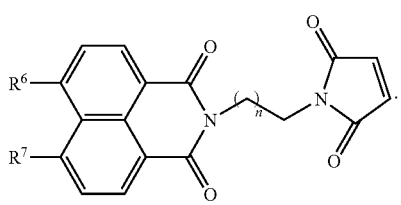

10. The article of claim 9, wherein the compound has a formula (IX):

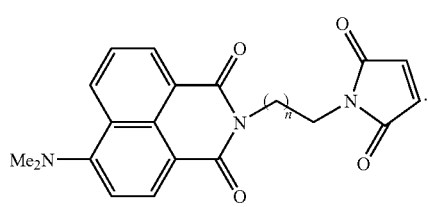

11. The article of claim 10, wherein n is 0.
12. The article of claim 10, wherein n is 1.
13. The article of claim 10, wherein n is 2.
14. The article of claim 7, wherein the compound has a formula (X):

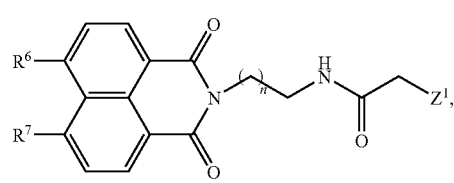

wherein $Z^1$ is halogen.

15. The article of claim 14, wherein the compound has a formula (XI):

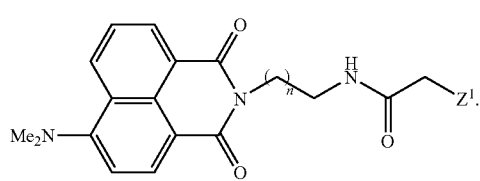

16. The article of claim 15, wherein n is 0.

17. The article of claim 15, wherein n is 1.
18. The article of claim 15, wherein n is 2.
19. The article of claim 15, wherein $Z^1$ is I.
20. The article of claim 15, wherein $Z^1$ is Br.
21. The article of claim 15, wherein $Z^1$ is Cl.
22. The article of claim 7, wherein the compound has a formula (XII):

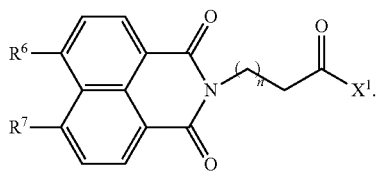

(XII)

23. The article of claim 1, wherein the article is a sensor.
24. An article, comprising:
a compound of formula (XIX):

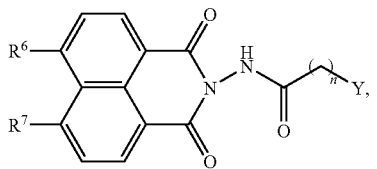

(XIX)

wherein $R^6$ and $R^7$ are independently hydrogen, halogen, alkyl, or —$NR^1R^2$ such that at least one of $R^6$ and $R^7$ is —$NR^1R^2$, $R^1$ and $R^2$ each independently being a substituted or unsubstituted alkyl;

Y is a halogen, —SH, —$NHR^3$, —$C(O)X^1$, -maleimidyl, —$NHCOR^3$, —$NHCO(CH_2)X^2$, or —$CH(NHR^3)COOH$;

$R^3$ is hydrogen, substituted or unsubstituted alkyl, or an N-protecting group;

$X^1$ is hydrogen, halogen, hydroxy, alkoxy, or O-succidimidyl;

$X^2$ is hydrogen, halogen, hydroxy, alkoxy; and n is 0, 1, 2, or 3.

25. The article of claim 24, wherein Y is a halogen.
26. The article of claim 24, wherein Y is Br.
27. An article, comprising:
a compound of formula (XX):

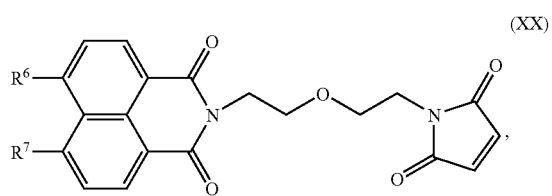

(XX)

wherein $R^6$ and $R^7$ are independently hydrogen, halogen, alkyl, or —$NR^1R^2$ such that at least one of $R^6$ and $R^7$ is —$NR^1R^2$, $R^1$ and $R^2$ each independently being a substituted or unsubstituted alkyl.

* * * * *

UNITED STATES PATENT AND TRADEMARK OFFICE
CERTIFICATE OF CORRECTION

| | | |
|---|---|---|
| PATENT NO. | : 8,440,835 B2 | Page 1 of 1 |
| APPLICATION NO. | : 12/449785 | |
| DATED | : May 14, 2013 | |
| INVENTOR(S) | : Barbara Imperiali et al. | |

It is certified that error appears in the above-identified patent and that said Letters Patent is hereby corrected as shown below:

In the Specification

Please replace the paragraph beginning on column 1, line 17, with the following paragraph:

--This invention was made with government support under Grant No. CHE0414243 awarded by the National Science Foundation and under Grant No. GM064346 awarded by the National Institutes of Health. The government has certain rights in this invention.--

Signed and Sealed this
Twenty-third Day of December, 2014

Michelle K. Lee
*Deputy Director of the United States Patent and Trademark Office*